(12) United States Patent
Brown et al.

(10) Patent No.: US 9,869,227 B2
(45) Date of Patent: Jan. 16, 2018

(54) SYSTEM AND METHOD FOR REPEATABLE FLUID MEASUREMENTS

(71) Applicant: Intellectual Reserves, LLC, Parker, TX (US)

(72) Inventors: Leon Brown, Parker, TX (US); Alvin R Wirthlin, Frisco, TX (US)

(73) Assignee: Intellectual Reserves, LLC, Parker, TX (US)

( * ) Notice: Subject to any disclaimer, the term of this patent is extended or adjusted under 35 U.S.C. 154(b) by 146 days.

(21) Appl. No.: 14/722,116

(22) Filed: May 26, 2015

(65) Prior Publication Data
US 2016/0349157 A1 Dec. 1, 2016

(51) Int. Cl.
*G01N 21/15* (2006.01)
*F01N 3/20* (2006.01)
*G01N 21/43* (2006.01)

(52) U.S. Cl.
CPC ............. *F01N 3/208* (2013.01); *G01N 21/15* (2013.01); *G01N 21/43* (2013.01); *F01N 2610/02* (2013.01); *F01N 2900/1814* (2013.01); *F01N 2900/1818* (2013.01); *G01N 2021/154* (2013.01); *Y02T 10/24* (2013.01)

(58) Field of Classification Search
CPC ........................................................ G01N 1/34
USPC ........ 73/60.11, 64.53, 64.56; 134/1, 1.3, 18, 134/57 R, 57 D, 113, 184, 186, 902
See application file for complete search history.

(56) References Cited

U.S. PATENT DOCUMENTS

| | | | |
|---|---|---|---|
| 4,640,616 A | 2/1987 | Michalik | |
| 5,166,752 A | 11/1992 | Spanier et al. | |
| 5,931,173 A * | 8/1999 | Schiele | B08B 3/00 134/113 |
| 6,286,929 B1 * | 9/2001 | Sharma | B41J 2/16552 347/27 |
| 6,350,007 B1 * | 2/2002 | Meichle | B41J 2/16552 347/27 |
| 6,643,021 B1 * | 11/2003 | Kawamura | G01N 21/15 356/436 |
| 6,816,248 B2 | 11/2004 | Sharma et al. | |
| 6,876,444 B2 | 4/2005 | Yilmaz et al. | |
| 6,890,390 B2 * | 5/2005 | Azar | B08B 3/12 134/1 |
| 7,027,138 B2 | 4/2006 | Larkin et al. | |
| 7,880,893 B2 * | 2/2011 | Ghislain | G01N 29/022 356/480 |
| 7,916,285 B2 | 3/2011 | Amamiya et al. | |
| 8,139,232 B2 | 3/2012 | Wolf et al. | |
| 8,284,389 B2 | 10/2012 | Forrer et al. | |
| 8,293,180 B2 | 10/2012 | Matsunaga et al. | |
| 8,605,271 B2 | 12/2013 | Wagner | |

(Continued)

*Primary Examiner* — Paul West
(74) *Attorney, Agent, or Firm* — Alvin R. Wirthlin

(57) ABSTRACT

A system for determining at least one property of a fluid and ensuring measuring surfaces of the system in contact with the fluid remain free of contaminants, includes a housing within which at least one measuring surface is located. The fluid to be measured flows through the housing and contacts the measuring surface. A signal generating device operably associated with the surface provides signals indicative of the at least one fluid property. A transducer is operably associated with the housing and causes agitation of the fluid flowing through the housing so that the measuring surface can be cleaned even during fluid measurement.

21 Claims, 21 Drawing Sheets

(56) References Cited

U.S. PATENT DOCUMENTS

| | | |
|---|---|---|
| 8,934,102 B2 | 1/2015 | Wirthlin et al. |
| 2008/0280371 A1 | 11/2008 | Anilkumar et al. |
| 2010/0327884 A1 | 12/2010 | McCall et al. |
| 2013/0242115 A1 | 9/2013 | Baba et al. |
| 2014/0116120 A1* | 5/2014 | Seckar .................. G01N 21/03 73/64.56 |

* cited by examiner

REFLECTION DATA

| Medium | 4-Burst Ave. (4 x 8 Lines) | 8-Line Ave. Deviation | Delta |
|---|---|---|---|
| De-ionized Water | 46,465 | +24 -51 | |
| 30.0% DEF | 16,208 | +71 -144 | Δ = 34,257 |
| 32.0% DEF | 10,857 | +40 -54 | Δ = 5,351 |
| 33.9% DEF | 9,581 | +12 -11 | Δ = 1,278 |

*FIG. 6*

COMBINED REFLECTION AND REFRACTION DATA

| Medium | 4-Burst Ave. (4 x 8 Lines) | 8-Line Ave. Deviation | Delta |
|---|---|---|---|
| De-ionized Water | 51,131 | +29  -29 | |
| 30.0% DEF | 25,688 | +47  -73 | Δ = 25,443 |
| 32.0% DEF | 17,719 | +36  -28 | Δ = 7,969 |
| 33.9% DEF | 9,019 | +52  -16 | Δ = 8,700 |

FIG. 9

SYSTEM AND METHOD FOR REPEATABLE FLUID MEASUREMENTS

BACKGROUND OF THE INVENTION

This invention relates to measurement devices, and more particularly to a system and method for determining the quality and other parameters of fluids and for dynamically ensuring repeatability of the measurements through in situ cleaning of measurement surfaces.

Transducers for measuring liquid level and other parameters are often used in vehicles, industrial equipment and other systems and components. The electrical output of such transducers change in response to a change in the liquid being measured, and is typically in the form of a change in resistance, capacitance, current flow, magnetic field, frequency, and so on. These types of transducers may include variable capacitors or resistors, optical components, Hall Effect sensors, strain gauges, ultrasonic devices, and so on.

In vehicles, industrial equipment and other systems powered by diesel fuel, a Selective Catalytic Reduction (SCR) system has been used to inject urea—a liquid-reductant agent—through a catalyst into the exhaust stream of a diesel engine. Urea sets off a chemical reaction that converts nitrogen oxides in the exhaust into nitrogen and water, which is then harmlessly expelled through the vehicle tailpipe. Previous urea quality sensor solutions have attempted to address industry quality control by ensuring that a specific quality of urea can be delivered into the exhaust gas stream. If the engine is operated without urea solution in the onboard urea tank, excessive NOx emissions can occur. Using a urea quality sensor, the SCR system can monitor the contents of the urea tank to alert an operator and/or system that the urea tank has been filled with other fluids, e.g., with tap water, coolant, windshield wiper fluid, oil, incorrect concentrations of urea solutions, and so on, instead of the correct concentration of urea solution. The introduction of a urea quality sensor into the SCR system also reduces the risk of tampering or accidental mis-filling and helps ensure compliance to environmental legislation, thus satisfying concerns of users and legislators alike. The urea quality sensor is intended to contribute to the overall success of SCR as a NOx reduction technology.

However, prior art solutions for measuring the presence or absence of the required urea concentration, such as refractive index measurements, capacitive, acoustic, and other known techniques, have been unable to measure the urea concentration with any degree of suitable accuracy to meet rigid industry and legislative requirements.

Moreover, the repeatability of such measurements has been lacking, even in laboratory-grade instrumentation, especially where the fluid quality and/or fluid properties are being measured under static conditions where it may be impractical to clean the measuring surfaces after each measurement, and more especially under continuous flow conditions where the system cannot be opened for cleaning, such as in above-mentioned SCR systems. Components of the fluid itself, undesirable contaminants present in the fluid through error or improper handling or filtering, as well as contaminants leaching into the fluid from surrounding surfaces in contact with the fluid can build up on measuring surfaces and cause a change in the measurement of the fluid, and thus lead to inaccurate results.

Besides contamination of the measuring surfaces associated with SCR systems, other fluids that may be measured, including but not limited to gasoline, oil, diesel fuel, coolant, and so on, associated with a vehicle, as well as other fluids in various industries, may also create undesirable deposits on the measuring surfaces, thus creating measurement errors.

It would therefore be desirous to provide a system and method for determining at least one fluid property including fluid quality, composition, and other parameters with a higher degree of accuracy than prior art systems in order to quantify whether or not proper fluid and/or the proper concentrations of fluids are being used in vehicles, machinery, and so on, while dynamically reducing or eliminating the collection of contaminants at least on measuring surfaces of the system.

BRIEF SUMMARY OF THE INVENTION

According to one aspect of the invention, a system for determining at least one property of a fluid includes: a housing for receiving the fluid to be measured; at least one measuring surface located in the housing and configured for contacting the fluid to be measured; a signal generating device associated with the at least one measuring surface for generating signals related to the at least one property of the fluid; and a cleaning device operably associated with the housing. The cleaning device generates waves that are transmitted through the fluid to be measured and to the at least one measuring surface to thereby remove undesired material from the at least one measuring surface.

According to a further aspect of the invention, a method for cleaning a measuring surface associated with a system for determining at least fluid property, with the system having a housing within which the measuring surface is located and through which the fluid can flow. The method includes generating high frequency pressure waves with a transducer to agitate the fluid flowing through the housing to be measured to thereby clean the measuring surface in contact with the fluid.

According to yet a further aspect of the invention, the method further includes locating a shifted resonant frequency of the transducer by driving the transducer over a sweeping range of driving frequencies to thereby effectively clean the measuring surface. The transducer over the sweeping range of driving frequencies during a first period of time to create a single burst of swept frequencies. In addition, the transducer can be driving with the single bursts of swept frequencies at discrete time intervals during a second period of time to thereby provide intermittent or continuous agitation of the fluid being measured for effective cleaning of the measuring surface.

BRIEF DESCRIPTION OF THE DRAWINGS

The foregoing summary as well as the following detailed description of the preferred embodiments of the present invention will be best understood when considered in conjunction with the accompanying drawings, wherein:

FIG. 6 is a chart showing sensor data obtained during actual measurement of different fluids and different concentrations of fluids;

FIG. 9 is a chart showing sensor data obtained during an actual measurement of different fluids and different concentrations of fluids with the system of the second embodiment as depicted in FIG. 4;

It is noted that the drawings are intended to depict only typical embodiments of the invention and therefore should not be considered as limiting the scope thereof. It is further noted that the drawings are not necessarily to scale. The invention will now be described in greater detail with reference to the accompanying drawings, wherein like designations denote like elements throughout the drawings.

DETAILED DESCRIPTION OF THE INVENTION

Figure 1:
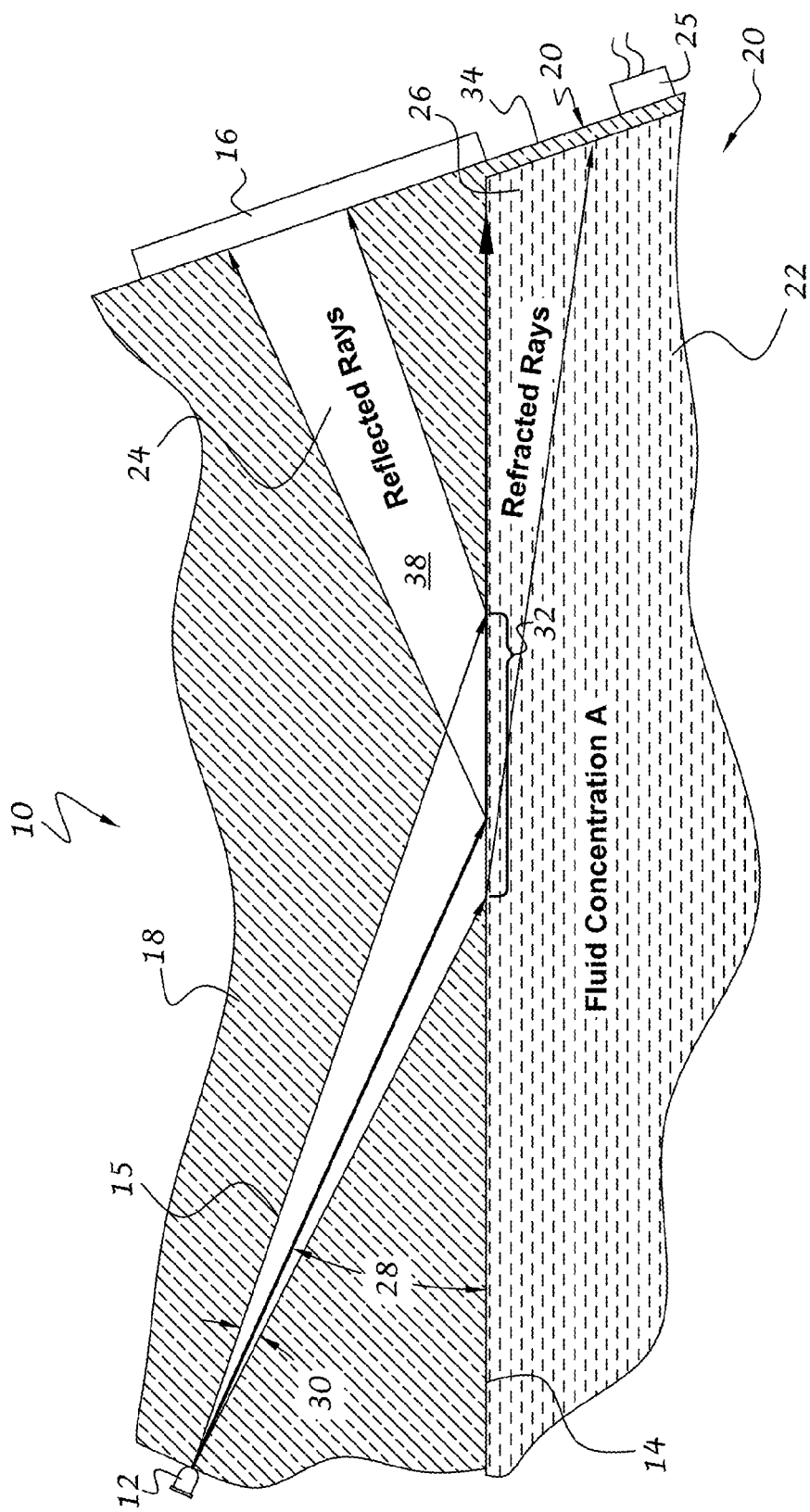
FIG. 1 is a diagrammatic view of a measurement system in accordance with the present invention when measuring the quality or other parameter(s) of a first fluid.

Referring to the drawings, and to FIG. 1 particular, a system 10 for measuring the quality of a fluid or solution, as well as other parameters, in accordance with the present invention is illustrated. Parameters that can be measured by the invention include, but are not limited to, the purity of a fluid or solution, the percentage or ratios of different fluids and/or solids within a solution, the refractive index of fluids, solutions, and/or solids, the absorption characteristics of fluids, solutions, and/or solids, the density of fluids and solutions, combinations thereof, and so on.

The system 10 preferably includes a light source 12 positioned for projecting radiant energy 15 through an optical body 18, a measuring surface 14 that abuts a reservoir 20 for holding a quantity of fluid 22, a signal generating device 16 for capturing reflected rays 24 and/or refracted rays 26 and generating signals based on the captured rays. The signal generating device 16 preferably comprises an optical sensor module 16 having a two-dimensional array of sensors for capturing reflected rays 24 and/or refracted rays 26 from the light source 12, and an embedded cleaning device 25 operably associated with the optical body 18 for automatically cleaning the measuring surface 14. The cleaning device 25 can be located on or within the optical body 18 or at another location spaced from the optical body and/or the measuring surface 14 where effective contactless cleaning of the measuring surface 14 can occur.

Although the present invention will be described with particular exemplary examples and data relating to the measurement or determination of a standardized aqueous urea solution comprising 32.5% high purity urea and 67.5% deionized water and variations thereof (often referred to as diesel exhaust fluid (DEF) or AdBlue), it will be understood that one or more parameters of virtually any fluid, combinations of fluids, solutions, semi-solids, and even solids can be measured with the fluid measuring systems as described herein, including without limitation fluid level, fluid quality, fluid composition, the amount and type of contaminants present in a fluid, and so on. It will be further understood that measuring surface(s) associated with various fluid measuring technologies that may come in contact with the fluid to be measured for determining such parameters can be remotely and automatically cleaned without departing from the spirit and scope of the invention, as will be described in greater detail below.

In accordance with an exemplary embodiment of the invention, the light source 12 is positioned for projecting the radiant energy 15 at a particular angle 28 with respect to the measuring surface 14. The particular angle 28 is largely dependent on the optical properties of the fluid being measured, such as the refractive index of the fluid. In accordance with one embodiment of the invention, where the ideal fluid 22 being measured is 32.5% laboratory grade urea in deionized water, the particular angle 28 is approximately equal to the critical angle (or the converse of the critical angle) as determined by a ratio of the refractive indices of the optical body 18 and the fluid 22. In addition, the light source 12 also projects radiant energy 15 at a cone angle 30 so that the radiant energy is distributed over a relatively large surface area 32 so that rays of light extend at angles less than, equal to, and greater than the critical angle (or converse to the critical angle). In this manner, a wide variety of different fluids, fluid combinations, solutions, semi-solids, and solids with different refractive indices can be measured.

The optical sensor module 16 can be in the form of a two-dimensional image sensor, such as a digital image module. The digital image module can be of a low-cost variety, having a particular number of pixels or independent sensors, commonly used in other mass-produced applications such as smart devices, mobile phones, touch pads, digital cameras, and so on. Under present market conditions, the sheer number of such modules produced in mass quantity can be taken advantage of in accordance with one aspect of the invention to produce a relatively low-cost measurement transducer with relatively high accuracy with respect to prior art solutions. A suitable image module may include, but is not limited to, a CMOS image sensor with a predetermined array of light sensitive sensors or pixels to capture either a virtual image of the surface area 32 either at the noted location or as projected on a diffuse surface 34 of the optical body 18 associated with the sensor 16. With this arrangement, lenses, mirrors, and/or other optical components are not needed, thus significantly reducing the number of parts, assembly time and other manufacturing costs, as well as their associated drawbacks (such as condensation, parallax errors, inherent defects in low-cost lenses, lens systems, mirrors, and so on). However, it will be understood that real image data can be captured and processed using one or more lenses and/or lens systems, mirrors, and other optical elements without departing from the spirit and scope of the invention. Regardless of the manner in which the image data is created (e.g. either real or virtual image creation), it will be understood that the image data can be processed in a similar manner to determine the fluid quality, as will be described in greater detail below with reference to FIGS. 5 and 15.

In accordance with an exemplary embodiment of the invention, an 8-bit CMOS monochrome digital image sensor chip was used to collect the data as shown in FIGS. 6, 7, 9, and 10 to measure and compare the parameters of different fluids. The exemplary digital image sensor has a resolution of 640 by 480 pixels (a matrix of 307,200 pixels), with each pixel capable of distinguishing and capturing 256 levels of visible light. It was found that such a module is suitable for capturing image data of the fluid to be measured, including subtle differences in fluid composition, to a relatively high degree of resolution. Accordingly, relatively high accuracy measurements have been obtained for determining the quality and/or type of the liquid being measured when compared with prior art solutions, as will be described in greater detail below. The digital image sensor chip is capable of operation at 15 frames per second (fps) or more in full resolution. The data captured during imaging can be transferred by any available data format such as a standard parallel digital video port (DVP) or by a single-lane MIPI high-speed serial interface with RAW pixel data, RGB, YUV, and/or Compressed Data outputs.

It will be understood that other image sensors with more or less resolution, color and/or black and white capabilities, as well as other image sensing technologies, such as charge-coupled devices (CCD's), one or more linear arrays, single or stand-alone optical sensors, such as photoresistors, photocells, phototransistors, photodiodes, photoconductors, and so on, as well as one or more arrays of single optical sensors can be used without departing from the spirit and scope of the invention.

The light source 12 preferably comprises a light emitting diode (LED), and both the light source and image module 16 can be surface-mount devices to efficiently optically couple the devices to the optical body 18. A shield or filter 36 (FIG. 3) or other light blocking member can be provided between the image module 16 and the light source 12 to prevent the direct transmission of stray light from the light source to the image module. It will be understood that other light sources can be used, such as, without limitation, incandescent bulbs, laser diodes, as well as any other source that emits radiant energy in one or more of the visible, ultra-violet, or infra-red spectrums.

It will be understood that the position of the light source and image module may be reversed or located at other positions without departing from the spirit and scope of the invention. In addition, the light source and/or the image module can be remotely located from the optical body 18 through the use of intermediate members such as optical fibers, transparent image conducting rods or fibers, lenses, or other suitable light guides.

Figure 2:
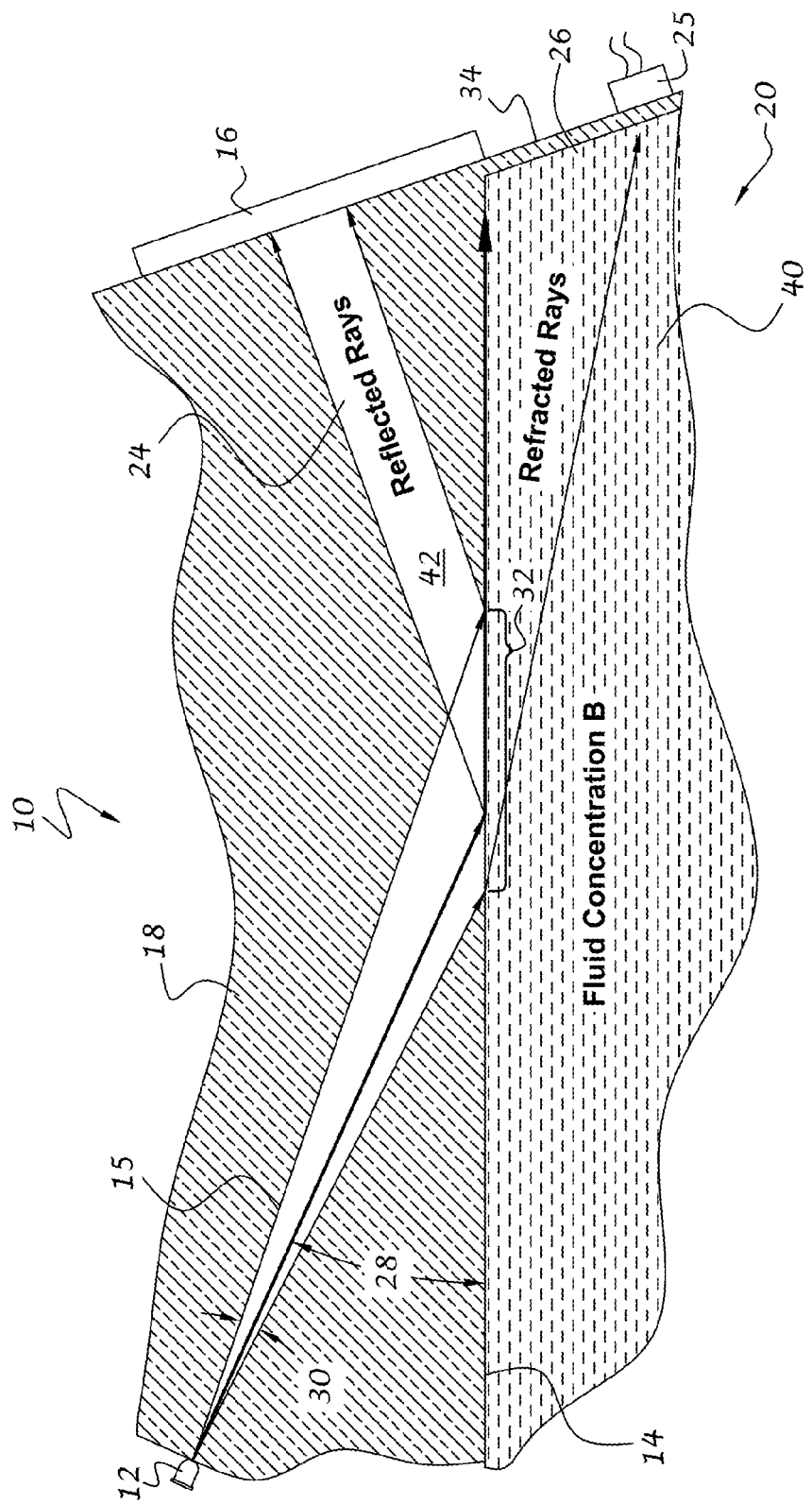
FIG. 2 is a view similar to FIG. 1 when measuring the quality or other parameter(s) of a second fluid different from the first fluid.

In use, as shown in FIG. 1, for a first fluid 22, the reflected rays 24 from the measuring surface 14 are directed towards the optical sensor module 16. Because of the refractive index of the fluid 22 and the refractive index of the optical body 18, a particular area 38 of reflected rays will be present. In contrast, as shown in FIG. 2, the area 42 of reflected rays is smaller than the area 38 of FIG. 1, due to the difference in the refractive index of the fluid 40. Accordingly, an area of the optical sensor module 16 exposed to the reflected rays will change from fluid to fluid. Since the sensed areas for each fluid is different, the optical sensor module 16 will output different signals which can be processed to determine whether or not the liquid being measured falls within acceptable parameters.

When the measuring surface 14 begins to collect contaminants or particles from the fluid being measured, the area of the optical sensor module 16 exposed to the rays may change due to the different refractive index and/or absorption of the reflected and/or refracted radiant energy, especially if the contaminants or particles have a different refractive index. This phenomena can occur even if there is no change in refractive index of the fluid itself, leading to incorrect measurement and subsequent processing of the fluid parameters. Accordingly, the cleaning device 25 can be operated continuously, intermittently, or at predetermined time intervals in order to ensure the measuring surface 14 remains clean or becomes clean at least to a level that is acceptable to the desired measurement accuracy.

The cleaning device 25 preferably comprises one or more ultrasonic transducers that generate ultrasonic waves between approximately 20 kHz and 400 kHz. When the ultrasonic transducer is driven at higher frequencies, it is capable of cleaning surfaces with more intricate detail than when driven at lower frequencies. The ultrasonic transducer 25 can be constructed of piezoelectric or magnetostrictive materials that can be driven at a predetermined frequency, discrete frequency steps, and/or sweeping frequencies in the ultrasonic bandwidth or at other effective frequencies, as will be described in further detail below.

In use, one or more transducers can be placed at one or more locations in the optic body, a housing (not shown) enclosing the optic body, and/or other locations where the fluid being measured is subjected to compression waves. The induced compression waves at ultrasonic frequencies in the fluid generated by the cleaning device 25 can induce millions of microscopic voids or cavitation bubbles in the fluid. Massive energy is generated when the cavitation bubbles collapse, resulting in a very large increase of pressure, which can be up to 20 kpsi or more, along with sudden increase in temperature of the fluid. However, since these changes occur in microscopic volumes, only the contaminants are removed from the measuring surface 14 and possibly surrounding surfaces without significantly changing the fluid properties, with the exception of perhaps the removed contaminants now immersed in the fluid at it flows through the housing. The measuring surface 14 can be cleaned ultrasonically during fluid flow, when the fluid is stopped, or at any other convenient time for cleaning or ensuring the cleanliness of the measuring surface.

Figure 3:
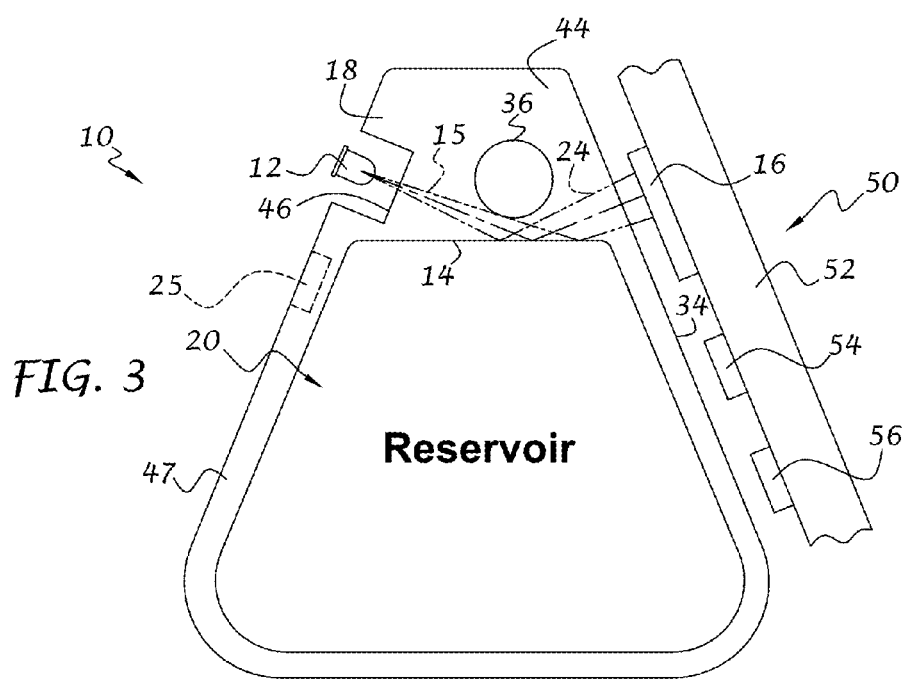
FIG. 3 is a top plan view of an exemplary measurement transducer assembly implementing the system of FIGS. 1 and 2 and including a sensor array and cleaning module for minimizing or eliminating contamination on measuring surface(s) that may affect the optical measurement in accordance with the invention.
Figure 4:
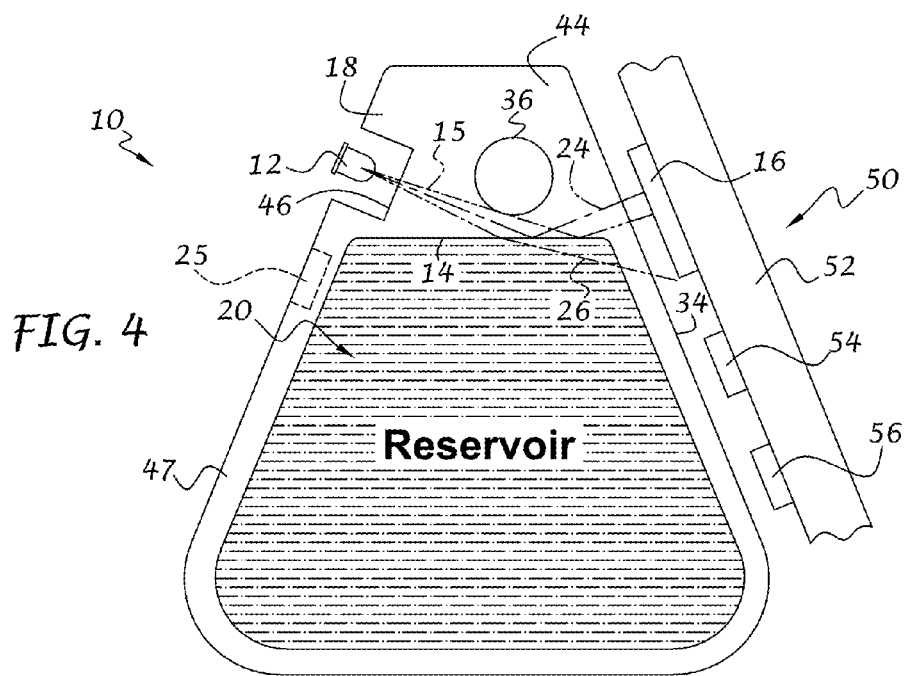
FIG. 4 is a top plan view of an exemplary measurement transducer assembly in accordance with a further embodiment of the invention showing a sensor array shifted to collected both reflection and refraction (absorption) data of different fluids, semi-solids or solids, and a cleaning module for minimizing or eliminating contamination on measuring surface(s) that may affect the optical measurement.

Turning now to FIGS. 3 and 4, the system 10 includes a measurement housing 44, given by way of example only, that incorporates the optical body 18 and includes the reservoir 20 for receiving the fluid to be measured, the measuring surface 14, the image surface 34 associated with the sensor 16, an aperture surface 46 associated with the light source 12, a light blocking opening 36 positioned between the aperture surface 46 and the image surface 34, and the cleaning device 25 installed in a side wall 47 of the measurement housing. In this exemplary embodiment, the cleaning device 25 is spaced from the measuring surface so that ultrasonic waves induced into the liquid being measured will clean the measuring surface 14. The housing can be constructed of any suitable material that minimizes damping of the ultrasonic waves when the cleaning device 25 is driven.

The image surface 34 can include a roughened surface, a lens material, or other surface conducive of forming an image from the reflected and/or refracted light associated with the measuring surface 14. In this manner, the need for one or more lenses is eliminated, thus reducing system costs and allowing the construction of a more compact measuring unit. Likewise, the aperture surface 46 preferably includes a small opening to permit radiant energy from the light source 12 to project therethrough at a particular cone angle. In this manner, a low-cost surface-mount LED or the like can be used without the need for focusing lenses or the like. In this manner, the system costs are further reduced and the measuring unit can be further compacted in size. The elimination of a lens at the light source also eliminates undesired lens defects and their consequent variations in light output from LED to LED, thus increasing the measurement accuracy of the system of the present invention.

The system 10 for measuring the quality of a fluid further includes an electronics section 50 with a printed circuit board (PCB) 52. The optical sensor module 16 is mounted on the PCB, as well as the light source 12 and other components such as a processor 54 and a signal conditioning module 56 connected to the processor for driving a display (not shown), the cleaning device 25, an audible signal device (not shown), and so on, based on signals from the processor. The processor can include means, such as software, circuitry, various electronic components, and so on, to process and analyze the captured digital image and determine one or more parameters of the fluid being measured based on the captured image. Data reflective of the liquid parameter(s) can be stored in a memory device and retrieved for signaling to a user, such as an operator, warranty entity, manufacturer, owner, fleet company, and so on, to indicate whether or not the proper DEF fluid has been put in the reservoir, and thus who may be at fault should a failure occur in the catalytic converter or other system components of the vehicle or diesel-powered equipment due to the use of improper fluid. Such data can also have a time/date stamp associated therewith to pinpoint the moment the improper fluid was added and/or used in the system, and thus who may be at fault when failure of one or more system components occurs.

It will be understood that data can be gathered in a similar manner, stored, and retrieved to indicate whether or not other automotive-type fluids (besides DEF) associated with vehicles or machinery, such as fuel, oil, windshield washer fluid, antifreeze, brake fluid, transmission fluid, and so on, are or were inside or outside of specified parameters or quality when first produced and/or introduced into the vehicle, machine, or other system. Thus, capturing data and warning an operator of potential catastrophic damage, as well as recording the introduction of improper fluids for determining who's at fault under warranty and/or repair situations, are made possible by the system 10 of the invention. It will be further understood that the present invention can be applied to non-automotive fluids, such as processing fluids, medical industry fluids, beverages, and so on, without departing from the spirit and scope of the invention.

Figure 5:
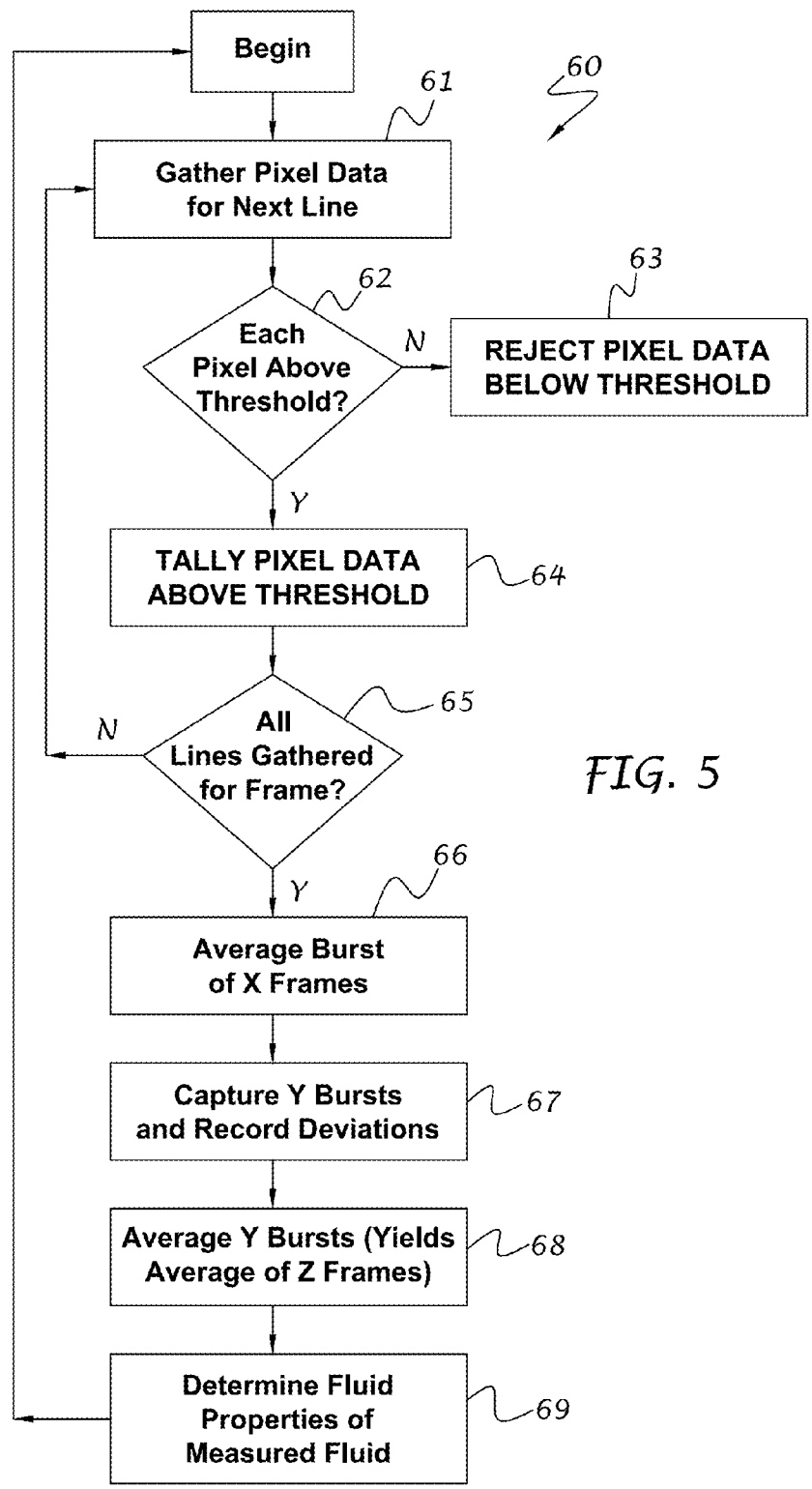
FIG. 5 is an exemplary algorithm for measuring and capturing sensor data related to the measurement system in accordance with the invention.

Referring now to FIGS. 3-5, a method 60 (FIG. 5) for processing data gathered by the optical sensor module 16 is illustrated. The method 60 includes first taking a snapshot or frame of the image projected onto the image surface 34 or the image as seen at the area 32 (FIGS. 1 and 2). The snapshot can be taken by gathering pixel data for each line of a frame (block 61), which can include a predefined area, the entire area, or a dynamically determined area of the optical sensor module 16. Each line of pixel data is then analyzed at block 62 to determine if each pixel is above a predetermined or dynamically determined brightness threshold. For example, in the exemplary embodiment having an optical sensor module in the form of a CMOS monochrome digital image sensor chip with a resolution of 640 by 480 pixels with each pixel capable of distinguishing and capturing 256 levels of visible light, the predetermined brightness threshold may be set at level 120. It will be understood, of course, that the brightness level threshold for the exemplary embodiment can be set in the range from 1 to 256 depending on the particular parameters of the optics and the fluid being measured. If, in block 62 the pixel value is below the predetermined brightness threshold value, it is discarded at block 63. The term "discarded" as used herein can mean that the pixels that fall below the predetermined value are held or stored in memory or storage, but not used for the present processing method, or that the pixel values are erased from memory or storage. If the rejected pixels are held in memory or storage, they may be subsequently used in further processing methods to determine further information, such as image shifting where the amount of shifting is a function of the refractive index of the fluid being measured, or other characteristics of the fluid being measured. At block 64, the pixel data for all pixels with a brightness value at or above the predetermined brightness threshold for the line of pixels just gathered is added. At block 65, it is determined whether or not all lines from the entire frame or predefined area(s) therefrom have been gathered. If not, the next line of pixel data is gathered at block 61. If all lines of the frame or frame portion have been gathered and tallied, then an average brightness value of the frame or frame portion is calculated. This process is repeated until the average brightness values of a predetermined number of frames or frame portions have been obtained. It will be understood that all data may be gathered then tallied together rather than tallying each separate line as described above. However, the single line method is preferred as it increases processing speed and preserves processor memory. At block 66, a predetermined number of frames are averaged, such as eight frames for example, after excluding the first frame, which may not have good data integrity. At block 67, a predetermined number of bursts (each burst representing the predetermined number of frames) are captured, such as four bursts for example, and the deviations of the four bursts are recorded. At block 68, the predetermined number of bursts (in this example four bursts) are averaged to thereby yield an average of 32 frames, for example, when eight frames are included in each burst. This step can be completed over a time interval of several milliseconds then repeated again for subsequent measurements. In this manner, a total pixel brightness value or pixel count value can be registered and used to a high degree of accuracy to determine whether or not the fluid being measured falls within acceptable parameters, as shown at block 69. It will be understood that more or less lines, frames, and/or bursts can be used without departing from the spirit and scope of the invention. It will be further understood that a pixel count, i.e. the number of pixels above the brightness threshold value, can be used in addition or alternatively to determine the fluid properties.

When it is determined that the measuring surface should be cleaned or maintained, whether it be through the optical sensor module 16, a designated portion thereof, a separate sensor (not shown) monitoring the cleaning surface, or at predetermined intervals based on operating time, fluid flow, down time, combinations thereof, and so on, the cleaning module 25 is activated to ensure that contaminants, constituents of the fluid, foreign particles, and so on, that may be on the measuring surface, or may potentially adhere to the measuring surface, are substantially reduced or eliminated to ensure that the determination of fluid properties are not negatively influenced by false readings due to a compromised measuring surface. An exemplary method for implementing the cleaning cycle or routine for the optical measuring surface as well as other measurement and non-measuring surfaces will be described below with respect to FIG. 25. In accordance with the invention, the fluid being measured also functions as the cleaning fluid to prevent, substantially reduce, or eliminate film formation on the measuring surface 14 of the optical body 18.

It will be understood that other processing methods can be used in addition or alternatively to the above-described techniques. In particular, an area of pixels that are above (or below) the threshold value can be analyzed to determine further fluid properties. Moreover, the light source 12 can include multiple light sources with different wave lengths or a single light source capable of projecting radiant energy at various wavelengths to obtain a spectral pattern for a particular fluid and determine its properties.

The techniques and methods discussed herein and as defined by the appended claims can be implemented in digital electronic circuitry, or in computer hardware, firmware, software, or combinations thereof. Apparatus may be implemented in a computer program product tangibly embodied in a machine-readable storage device for execution by a programmable processor, and the methods described herein may be performed by a programmable processor executing a program of instructions to perform functions by operating on input data and generating output. Further embodiments may advantageously be implemented in one or more computer programs that are executable on a programmable system including at least one programmable processor coupled to receive data and instructions from and transmit data and instructions to a data storage system, at least one input device, and at least one output device. Each computer program may be implemented in a high level procedural or object-oriented programming language, or in assembly or machine language, which can be compiled or interpreted. Suitable processors include, by way of example, both general and special purpose microprocessors. Generally, a processor receives instructions and data from read-only memory and/or RAM. Storage devices suitable for tangibly embodying computer program instructions and data comprise all forms of non-volatile memory including, by way of example and not by limitation, semiconductor memory devices, such as EPROM, EEPROM, and flash memory devices; magnetic disks such as internal hard disks and removable disks; magneto-optical disks; CD-ROM disks, solid state drives, and so on. Any of the foregoing may be supplemented by, or incorporated in, specially designed application specific integrated circuits (ASICs).

Figure 7:
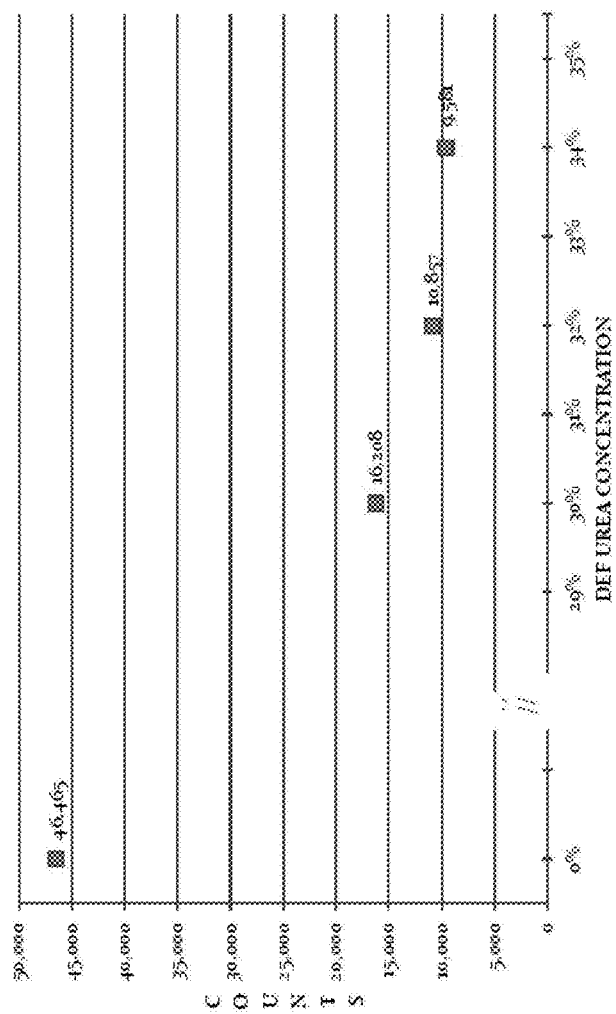
FIG. 7 is a graph showing the sensor data of FIG. 6.

Turning now to FIGS. 6 and 7, reflection information, in the form of pixel counts above the threshold brightness value were obtained during actual measurements using the setup of FIGS. 3 and 4, with the absence of the cleaning module 25, yet with manually maintaining a clean measuring surface. In particular, it was found that deionized water used during the measurements had 46,465 pixels above the threshold value. Likewise, it was determined that diesel exhaust fluid (DEF) having a solution of 30% laboratory grade urea in distilled water had 16,208 pixels above the threshold value. A difference between the pixel counts of the deionized water and 30% DEF solution was 34,257. Accordingly, deionized water was easily distinguishable from the 30% DEF solution. In addition, it was determined that DEF having a solution of 32% laboratory grade urea in distilled water had 10,857 pixels above the threshold value. A difference between the pixel counts of the 30% DEF solution and 32% DEF solution was 5,351. Likewise, it was determined that DEF having a solution of 33.9% laboratory grade urea in distilled water had 9,581 pixels above the threshold value. A difference between the pixel counts of the 32% DEF solution and 33.9% DEF solution was 1,278. This was accomplished using an optical sensor module having a 640 by 480 sensor (pixel) array. It has been found that much larger differences are achieved with higher resolution optical sensor modules, as will be described in greater detail below.

Figure 8:
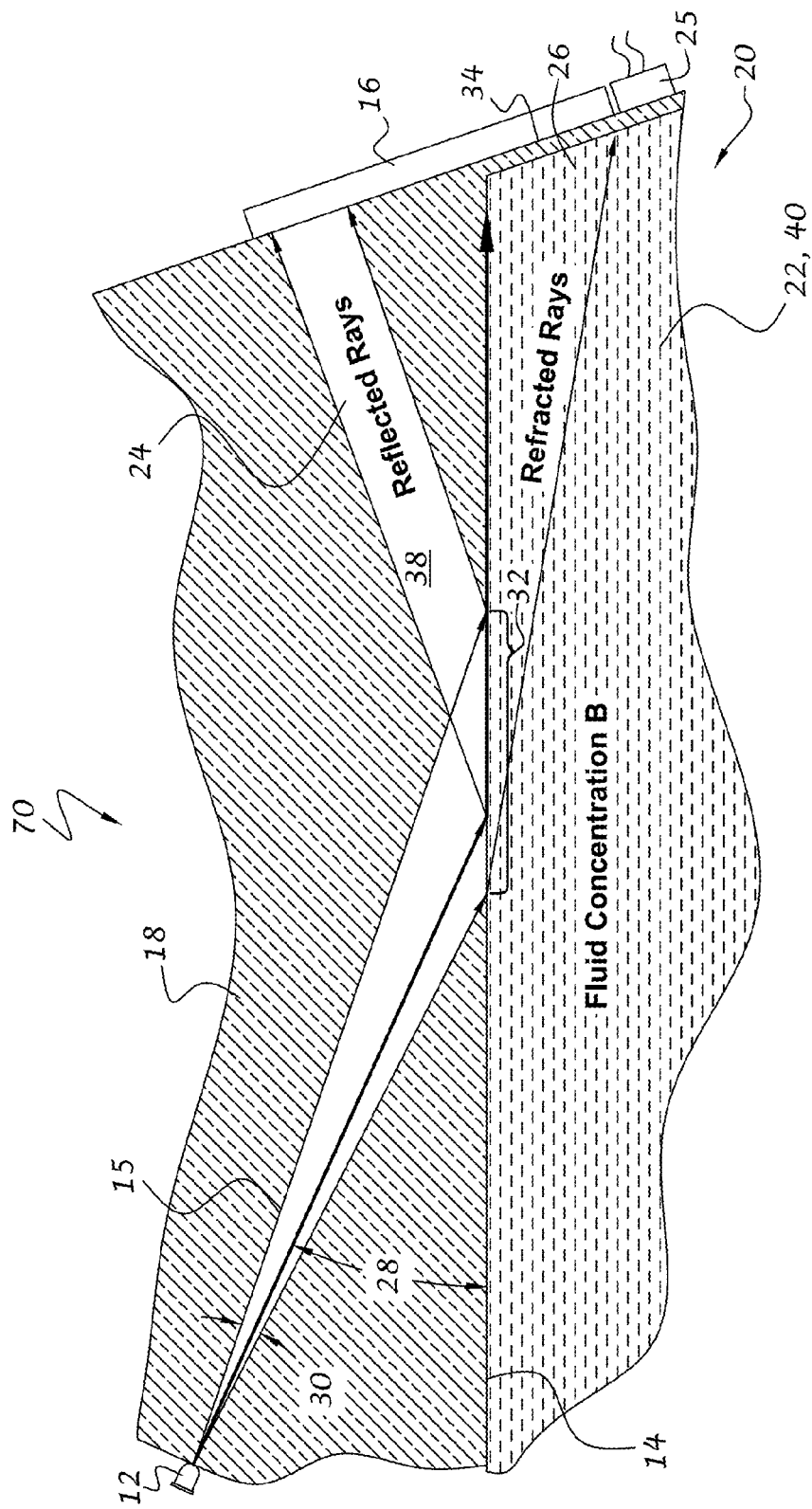
FIG. 8 is a diagrammatic view of a measurement system in accordance with the FIG. 4 embodiment to obtain reflection and refraction (absorption) data.

Referring now to FIG. 8, a system 70 for measuring the quality of a fluid, as well as other parameters, in accordance with a further embodiment of the present invention is illustrated. The system 70 is similar in construction to the system 10 previously described, with the exception that the optical sensor module 16 is shifted along the image surface 34 to obtain data related to both the reflected rays 24 traveling through the optical body 18 and the refracted rays 26 traveling through the fluid being analyzed, such as fluid 22 or fluid 40 (FIGS. 1 and 2). As in the previous embodiment, the pixel count is obtained, but this time for the pixels whose brightness value is above one or more predetermined or dynamic threshold brightness values. For example, the threshold value of the reflected rays may be the same or different from the threshold value of the refracted rays. As in the previous embodiment, it will be understood that other processing techniques can be used in addition or alternatively to the above-described technique of the present invention. For example, one or more areas of pixels that are above the threshold value can be analyzed to determine further fluid properties. Moreover, the light source 12 can include multiple light sources with different wave lengths or a single light source capable of projecting radiant energy at various wavelengths to obtain a spectral pattern for a particular fluid and determine its properties.

Figure 10:
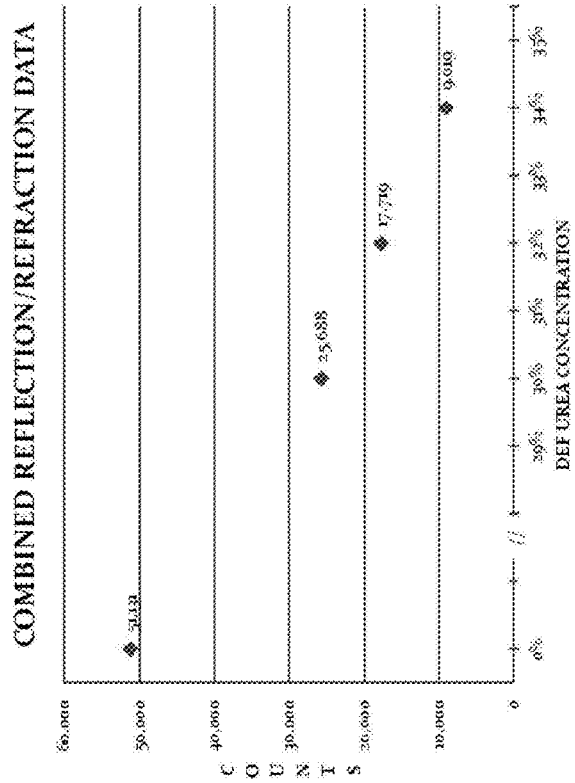
FIG. 10 is a graph showing the sensor data of FIG. 9.

Turning now to FIGS. 9 and 10, both reflection and refraction information, in the form of pixel counts above the threshold brightness value were obtained during actual measurements using the setup of FIGS. 3 and 4, but with the optical sensor module 16 shifted as shown in FIG. 8. In particular, it was found that deionized water had 51,131 pixels above the threshold value. Likewise, it was determined that DEF having a solution of 30% laboratory grade urea in distilled water had 25,688 pixels above the threshold value. A difference between the pixel counts of the deionized water and 30% DEF solution was 25,443. Accordingly, deionized water was easily distinguishable from the 30% DEF solution. In addition, it was determined that DEF having a solution of 32% laboratory grade urea in distilled water had 17,710 pixels above the threshold value. A difference between the pixel counts of the 30% DEF solution and 32% DEF solution was 7,969. Likewise, it was determined that DEF having a solution of 33.9% laboratory grade urea in distilled water had 9,019 pixels above the threshold value. A difference between the pixel counts of the 32% DEF solution and 33.9% DEF solution was 8,700. This was accomplished using the same optical sensor module having a 640 by 480 sensor array. Again, it has been found that much larger differences can be achieved with higher resolution optical sensor modules. From the graph shown in FIG. 10, it is apparent that the combined technique of detecting the pixel count for both reflected and refracted light rays produces a more linear output.

Thus, the approximate difference of 8,000 pixels between two percentage points of the DEF concentration is both surprising and significant. In prior art devices and techniques, arriving at the capacity to distinguish between a single percentage in DEF concentration has been extremely difficult and, as far as the prior art is understood, has not been achieved until the present invention. Thus, in accordance with the present invention, a pixel count, and thus a measurement count, of approximately 4,000 points between a single percent change in DEF solution is now possible, giving a potential accuracy of measuring DEF down to 0.025% concentration using a 640×480 sensor array. This is a significant improvement over the greater than +/−2% accuracy of prior art solutions. Again, it has been confirmed that the use of sensor arrays with higher resolution in accordance with the invention has led to significantly greater accuracy of determining the fluid quality without a significant increase in cost.

It will be understood that measurement of the Urea concentration in DEF is only one example as one or more parameters of virtually any fluid, combinations of fluids, semi-solids, and even solids can be measured with the fluid measuring systems as described herein without departing from the spirit and scope of the invention.

Figure 11:
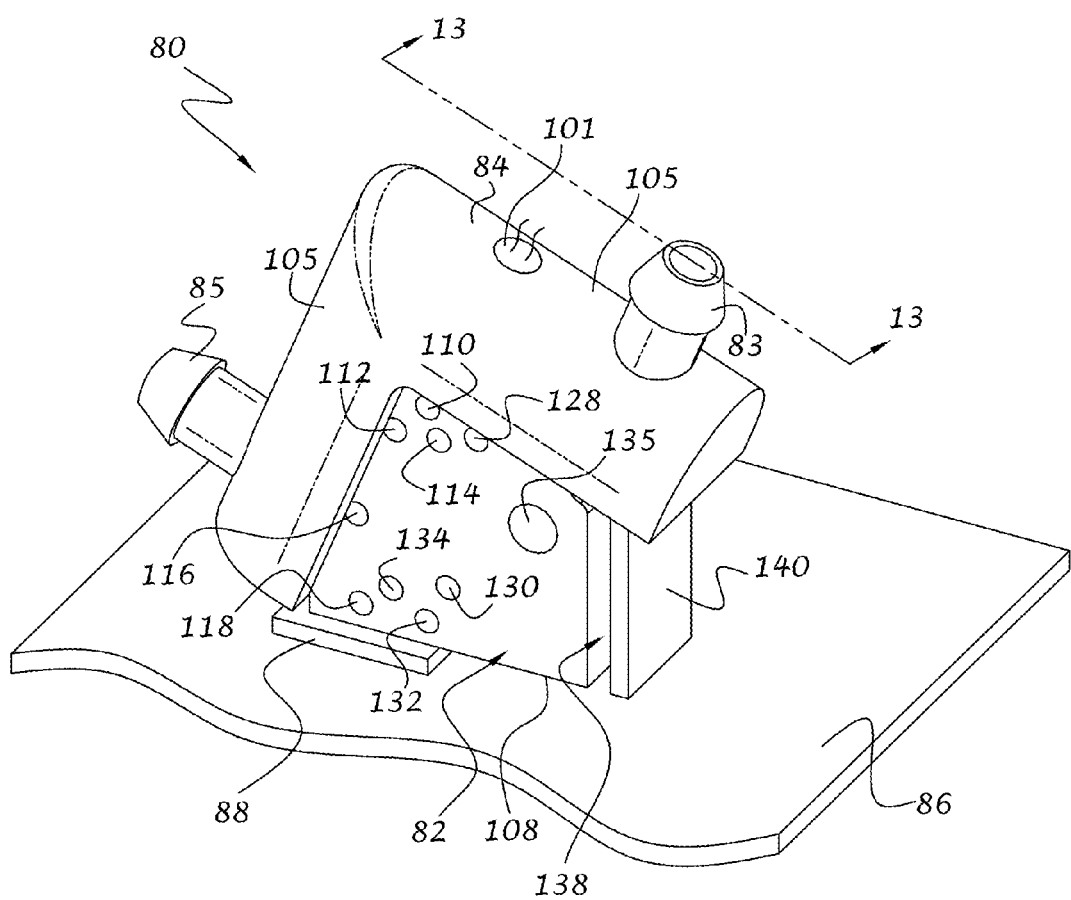
FIG. 11 is an isometric view of an exemplary measurement transducer assembly incorporating a sensor array and cleaning module for minimizing or eliminating contamination on measuring surface(s) that may affect the measurements in accordance with a further embodiment of the invention.
Figure 12:
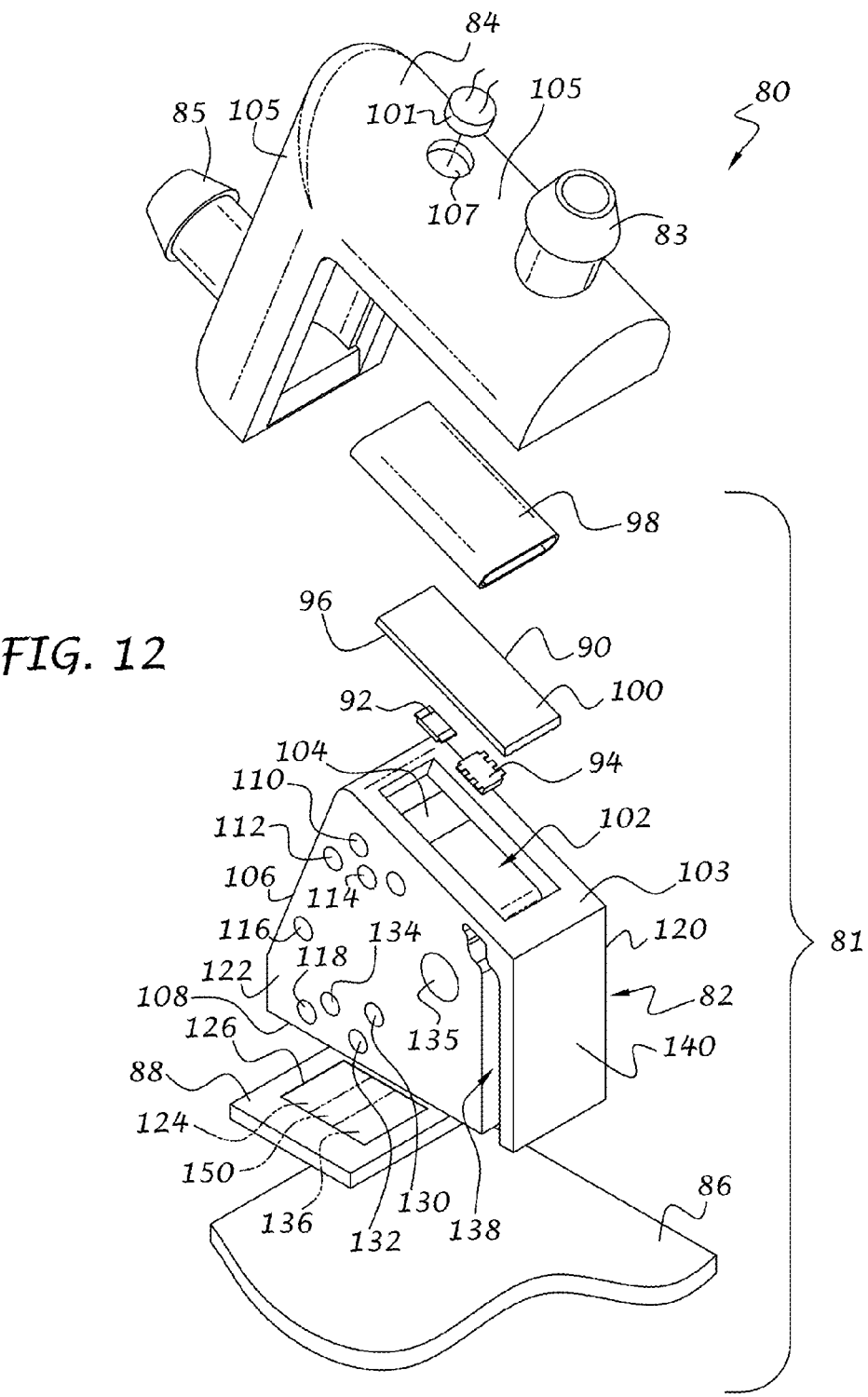
FIG. 12 is an exploded isometric view thereof.
Figure 13:
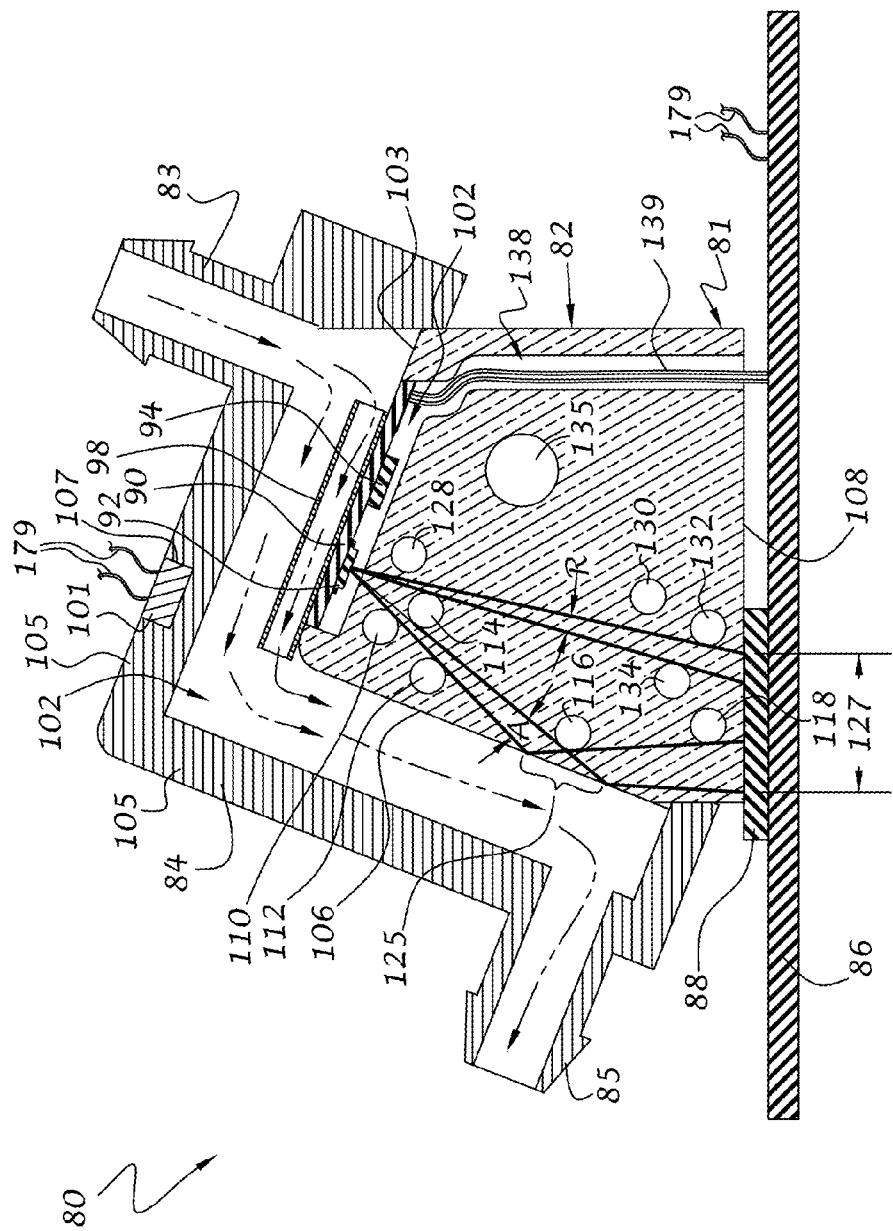
FIG. 13 is a sectional view of the transducer assembly taken along line 13-13 of FIG. 11 and diagrammatically showing light paths of a light source of the sensor assembly and the location of the cleaning module.

Referring now to FIGS. 11 to 13, a system 80 for measuring the quality of a fluid, as well as other parameters, in accordance with yet a further embodiment of the present invention is illustrated. The system 80 preferably includes an optical measurement assembly 81 having an optical body 82 connected to a housing 84 that may be configured for inline, in-tank-, or in-tank-head measurement systems to thereby measure the quality and/or type of a fluid as it is being transferred from one location to another, such as for example from a DEF tank to a catalytic converter or other part of a SCR system; from a filling station to the DEF tank; from the DEF tank and back into the DEF tank, and so on. To that end, an input barb 83 and an output barb 85 can be associated with the housing 84 for connection of tubing or the like to transport the fluid to be measured through the housing 84 and across the optical body 82.

As with the previous systems, it will be understood that one or more parameters of virtually any fluid, combinations of fluids, semi-solids, and even solids can be measured with the fluid measuring system described herein without departing from the spirit and scope of the invention.

The system 80 includes a primary PCB 86 with a signal generating device 88, preferably comprising an optical sensor module, that is positioned with respect to the optical body 82 for determining various fluid parameters as described with the previous embodiments. The optical sensor module 88 can be a surface-mount device to save space and optically couple with the optical body without the need for lenses or other optical parts or optical assemblies. Other components associated with the PCB and the system 80 will be described with reference to FIG. 14 below.

As best shown in FIGS. 12 and 13, the optical measurement assembly 81 further includes a secondary PCB 90 with a light source 92, such as a surface-mount LED, is connected to the bottom or inner surface 96 of the secondary PCB 90. A temperature sensor 94 is also mounted on the bottom surface 96 and a heat sink 98 is thermally connected to the top or outer surface 100 of the secondary PCB. The heat sink 98 is oval in shape, as shown in FIG. 12, but may be of any suitable shape and include cooling or radiating fins (not shown). The heat sink 92 is in a fluid flow path of the sealed interior 102 (FIG. 13) located between the optical body 82 and the housing 84 so that the temperature of the fluid to be measured is at least partially stabilized as it passed through and around the heat sink 92. The secondary PCB is preferably sufficiently thin so that differences in temperature between the outer and inner surfaces are minimized. In this manner, the temperature of the fluid to be measured can be ascertained to a high degree of accuracy, depending on the type of temperature sensor selected. The temperature sensor 94 may alternatively be mounted to the outer surface 100 to be in more direct contact with the fluid to be measured without departing from the spirit and scope of the invention.

A channel or conduit 138 is formed in the side surface 122 of the optical body 82 for receiving an electrical cable 139 to thereby electrically connect the secondary PCB 100 to the primary PCB 86. Although the channel 138 is open from the side surface 122, it will be understood that the channel can be a closed conduit and/or formed at other locations on the optical body 82 or outside of the optical body as long as the primary and secondary PCB's are electrically connected together. A hole 135 is formed in the optical body 82 and extends between the side surfaces 120 and 122. The hole 135 is sized to receive a threaded fastener or the like for mechanically connecting the optical body to housing structure. It will be understood that the hole 135 can be eliminated and that the optical body 182 can be connected to suitable structure through any well-known connection means such as adhesive bonding, clamping, fastening, ultrasonic welding, and so on.

A cleaning device 101 is positioned within a depression 107 formed in a wall 105 of the housing 84 at one or more locations and/or orientations with respect to the housing. Although the wall 105 is shown as integral with the housing 84, the wall can comprise a sheet of suitable material mounted over an opening in the housing and to which the cleaning device 101 is attached. The cleaning device 101 preferably comprises an ultrasonic transducer that is similar in construction to the cleaning device 25 for cleaning the measuring surface of the optical body 182 as previously described. As in the previous embodiment, the ultrasonic transducer can be driven at a predetermined frequency, discrete frequency steps, and/or sweeping frequencies in the ultrasonic bandwidth, as will be described in further detail below.

In use, one or more transducers can be placed at one or more locations in the wall 105 of the housing 84 and/or other locations where the optic, the measuring surface, the housing and/or the fluid is subjected to ultrasonic vibration so that particles, contaminants, film, layers, and the like that may tend to collect on, or be in the process of collecting on, the measuring surface can be ultrasonically cleaned during fluid flow, when the fluid is stopped, or at any other convenient time for cleaning or ensuring the cleanliness of the measuring surface. In accordance with the invention, the fluid being measured also functions as the cleaning fluid to prevent, substantially reduce, or eliminate film formation on the measuring surface 106.

The optical body 82 is preferably formed of transparent material, such as acrylic, polycarbonate, glass, crystal, or any other suitable material that is transparent or translucent to the radiant energy emitted by the light source and compatible with the fluid being measured within the range of operating or ambient temperatures. The optical body 82 includes a channel 102 formed in a top surface 103 thereof for receiving the secondary PCB 90 and the attached LED 92 and temperature sensor 94. The LED 92 is set at a position on the secondary PCB 90 to be in alignment with a window 104 formed in the channel 102 so that radiant energy from the LED can be directed towards both a front measuring surface 106 and a bottom surface 108 which faces the optical sensor module 88. The particular angle between the measuring surface 106 and the bottom surface 108 can greatly vary depending on the fluids to be measured and the amount of accuracy desired when measuring subtle differences between similar fluids under varying atmospheric conditions and/or variations in the contents of the fluid. By way of example, for DEF fluids having a concentration of urea in deionized water ranging from about 30% to 35%, the measuring surface 106 extends at an angle of about 68.5 degrees with respect to the bottom surface 108. Surprisingly, it has been found that very high accuracy can be obtained for measuring differences in the relatively narrow range of DEF fluids when taken in conjunction with a predefined measurement cone angle of radiant energy emanating from the light source.

It will be understood that the measuring surface 106 is not limited to a flat profile at the particular angle as shown and described, but can be oriented at any suitable angle and may comprise other shapes include concave or convex surfaces, multifaceted measuring surfaces, combinations thereof and so on, without departing from the spirit and scope of the invention.

A plurality of light blocking apertures 110, 112, 114, 116, and 118 are formed at predefined locations in the optical body and extend between the right side 120 and left side 122 thereof to direct light from the LED 92 towards a transparent window 125 (FIG. 13) formed on the measuring surface 106 (best shown in FIG. 13) which is then reflected and/or refracted towards the bottom surface 108, and thus to a measurement sensor array area 124 (FIGS. 12 and 16) of a "frame" or sensor array portion 126 of the optical sensor module 88. The amount of reflected and/or refracted radiation is proportional to the refractive index of the fluid being measured, and thus can greatly vary even for similar types of fluids.

Likewise, a plurality of light blocking apertures 128, 130, 132, and 134 are formed at predefined locations in the optical body 82 and extend between the right and left sides thereof to direct light, in conjunction with aperture 114, from the LED 92 towards the bottom surface 108, and thus to a reference sensor array area 136 (FIGS. 12 and 16) of the sensor array portion 126 of the optical sensor module 88. In this manner, the brightness of the light source can be constantly monitored by the reference sensor array area 136 which may be caused by changing atmospheric or environmental conditions, degradation of the light source over time, compensation for lower brightness when the power supply is in the form of a battery for portable measurement applications, and so on, so that any changes in the brightness of the light source measurement due to such conditions can be compensated for.

Preferably, the entire optical body 82, including the apertures 110, 112, 114, 116, 118, 128, 130, 132, and 134, as well as the hole 135, top surface 103, top channel 102, measuring surface 106, bottom surface 108, side surfaces 120 and 122, the rear surface 140, and the side channel 138 of the optical body 82 are coated with a dark layer of material such that radiant energy reaching the apertures, surfaces, and channels from the LED are at least substantially absorbed to prevent undesired radiant energy from reaching the sensor array portion 126 of the optical sensor module 88. The window 104 in the channel 102, as well as a window 125 (FIG. 13) on the measuring surface and a window 127 (FIG. 13) on the bottom surface 108 are formed by masking off areas on those surfaces of the optical body 82 prior to coating. The coating preferably comprises a dark dye material that penetrates a short distance into the optical body. The coating can additionally or alternatively comprise dark paint or other materials that absorb undesirable light. Other coatings may also be used, including hydrophobic and/or oleophobic coatings, in order to reduce or eliminate contamination on the window areas of the optical body 82 that may otherwise be left by the fluid.

Since the preferred light source is a low-cost surface-mount LED without a lens (to avoid inaccuracies that may otherwise be introduced by variations in lens geometry of mass-produced LED's), the expanding radiant energy from the light source can be precisely controlled. For example, the thick lines 142, 144 in FIG. 13 represent a cone angle or otherwise divergent angle "A" of measurement light from the LED that is defined by the locations of the apertures 110, 114, 112, and 16, while a divergent reflective angle of the reflected light from the measuring surface 106 is controlled by the apertures 116 and 118. Likewise, a cone angle or otherwise divergent angle "R" of the reference light (represented by the thick lines 146 and 148 in FIG. 13) from the same LED can be precisely controlled by the locations of the apertures 128, 114, 130, and 134. By way of example, the diverging beam of the "active" or measurement light can have an active angle "A" of approximately +/−three degrees while the diverging beam of the "reference" light can have a reference angle "R" of approximately +/−five degrees. Thus, as in the previous embodiment, radiant energy projects onto the measuring surface at the predefined area so that the rays of light extend at angles less than, equal to, and greater than the critical angle (or converse to the critical angle) between the optical body and the fluid to be measured.

It will be understood that the angles of diverging light can greatly vary depending on the angle or inclination of the measuring surface 106 with respect to the bottom surface 108 and the particular fluid(s) to be measured. Accordingly, the diverging light spray from the LED that would otherwise extend over a relatively large angle, can be controlled without the radiant energy being directed through lenses, aperture plates, or other optical components, thereby reducing the number of parts, inaccuracies due to tolerance accumulations, and so on. However, it will be understood that such optical devices can be used in conjunction with the methods of the invention for determining one or more parameters of the fluid being measured.

It will be understood that the apertures can be replaced with slots or other light directing features without departing from the spirit and scope of the invention. By way of example, the material between apertures 110 and 112 can be removed to form an elongate slot extending through the optical body 82. Likewise, the material between apertures 114, 116, 118, and 134 can be removed to form a triangular-shaped slot between the measurement light rays and the calibration light rays. It will be apparent that other slots can extend between other aligned apertures.

In accordance with one embodiment of the invention, where the ideal fluid 22 being measured is 32.5% laboratory grade urea in deionized water, the particular angle 28 is approximately equal to the critical angle (or the converse of the critical angle) as determined by a ratio of the refractive indices of the optical body 82 and the fluid to be measured. In addition, the light source 92 also projects radiant energy 15 at a cone angle 30 so that the radiant energy is distributed over a relatively large surface area 32 so that rays of light extend at angles less than, equal to, and greater than the critical angle (or at angles converse to the critical angle). In this manner, a wide variety of different fluids, fluid combinations, semi-solids, and solids with different refractive indices can be measured.

With this arrangement, lenses, mirrors, and/or other optical components are not needed, thus significantly reducing the number of parts, assembly time and other manufacturing costs, as well as their associated drawbacks (such as condensation, parallax errors, inherent defects in low-cost lenses, lens systems, mirrors, and so on). However, it will be understood that real image data can be captured and processed using one or more lenses and/or lens systems, mirrors, and other optical elements for analyzing the fluid in accordance with the measurement methods of the invention. Regardless of the manner in which the image data is created (e.g. either real or virtual image creation), it will be understood that the image data can be processed in a similar manner to determine the fluid quality, as discussed above with respect to FIG. 5 and as will be discussed below with reference to FIG. 15.

The optical sensor module 88, as in the previous embodiment, is preferably in the form of a two-dimensional image sensor, such as a digital image module. The digital image module can comprise a relatively low-cost device, having a particular number of pixels or independent sensors, commonly used in other mass-produced applications such as smart devices, mobile phones, touch pads, digital cameras, and so on. A suitable image module may include, but is not limited to, a CMOS image sensor with a predetermined array of light sensitive sensors or pixels to capture an image of the measuring surface area as defined by the measurement window 125. The sensor array portion 126 preferably includes a dark or calibration sensor array area 150 (FIG. 16) located between the measurement sensor array area 120 and reference sensor array area 126. The dark sensor array area 150 is at least substantially void of light so that variations in signals from the third sensor array area are not affected by light but rather of the response of the sensor array portion 126 under varying conditions independent of light, such as such as temperature, pressure, humidity, and so on. Accordingly, errors produced by the optical sensor module 88 can be monitored and compensated for independent of variations in light that may be present at the first and second sensor array areas.

Figure 16:
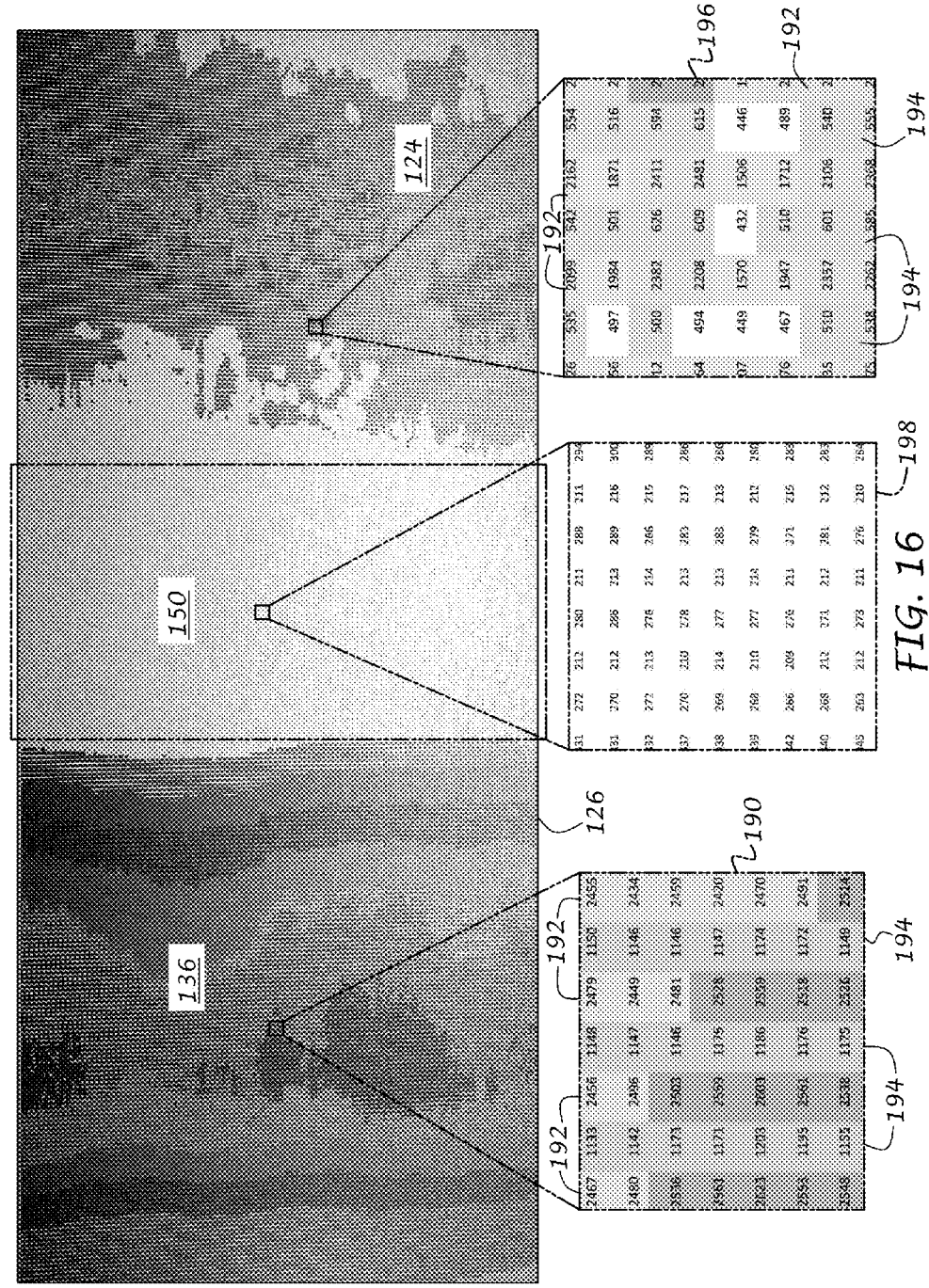
FIG. 16 shows actual data gathered by the measurement transducer of FIG. 11 and displayed in a spreadsheet wherein a value of each pixel and corresponding color assigned to a range of values are associated with separate cells of the spreadsheet in accordance with corresponding pixel locations in the sensor array.

In accordance with an exemplary embodiment of the invention, a 12-bit CMOS color digital image sensor chip was selected for the optical sensor module 88 and was used to collect the data as shown in FIG. 16. The exemplary digital image optical sensor module has a resolution of 5 megapixels with a matrix of 2,592×1,944 pixels. Each pixel is capable of distinguishing between 4,096 different brightness levels of visible light. The matrix of pixels can follow a Bayer pattern with alternating rows of green and red pixels and blue and green pixels. The digital image sensor is also capable of operation at 15 frames per second (fps) in full resolution. A suitable digital image sensor that meets this configuration is known at the MT9P004 by Aptina™. However, it will be understood that the particular digital image sensor can vary greatly in resolution, may have lower or higher detection levels of brightness, and may have other configurations or patterns of red, blue and green pixels. It will be further understood that the digital image sensor can be a monochrome device, as discussed in the previous embodiment, or may include a matrix of analog optical sensors or a linear array of analog or digital optical sensors. In some cases, in accordance with a further embodiment of the invention, the optical sensor can comprise a single analog or digital sensor.

With the exemplary optical sensor module 88 having a resolution of 5 megapixels and 4,096 brightness levels per pixel, it was found that image data of the fluid being measured can be captured to a very high degree of resolution when compared to prior art devices, as will be described below with reference to FIG. 16. Accordingly, very high accuracy measurements have been obtained for determining the type and/or quality of the measured fluid when compared with prior art solutions. As in the previous embodiment, the data captured during imaging can be transferred by any available data format such as a standard parallel digital video port (DVP) or by a single-lane MIPI high-speed serial interface with RAW pixel data, RGB, YUV, and/or Compressed Data outputs.

Figure 14:
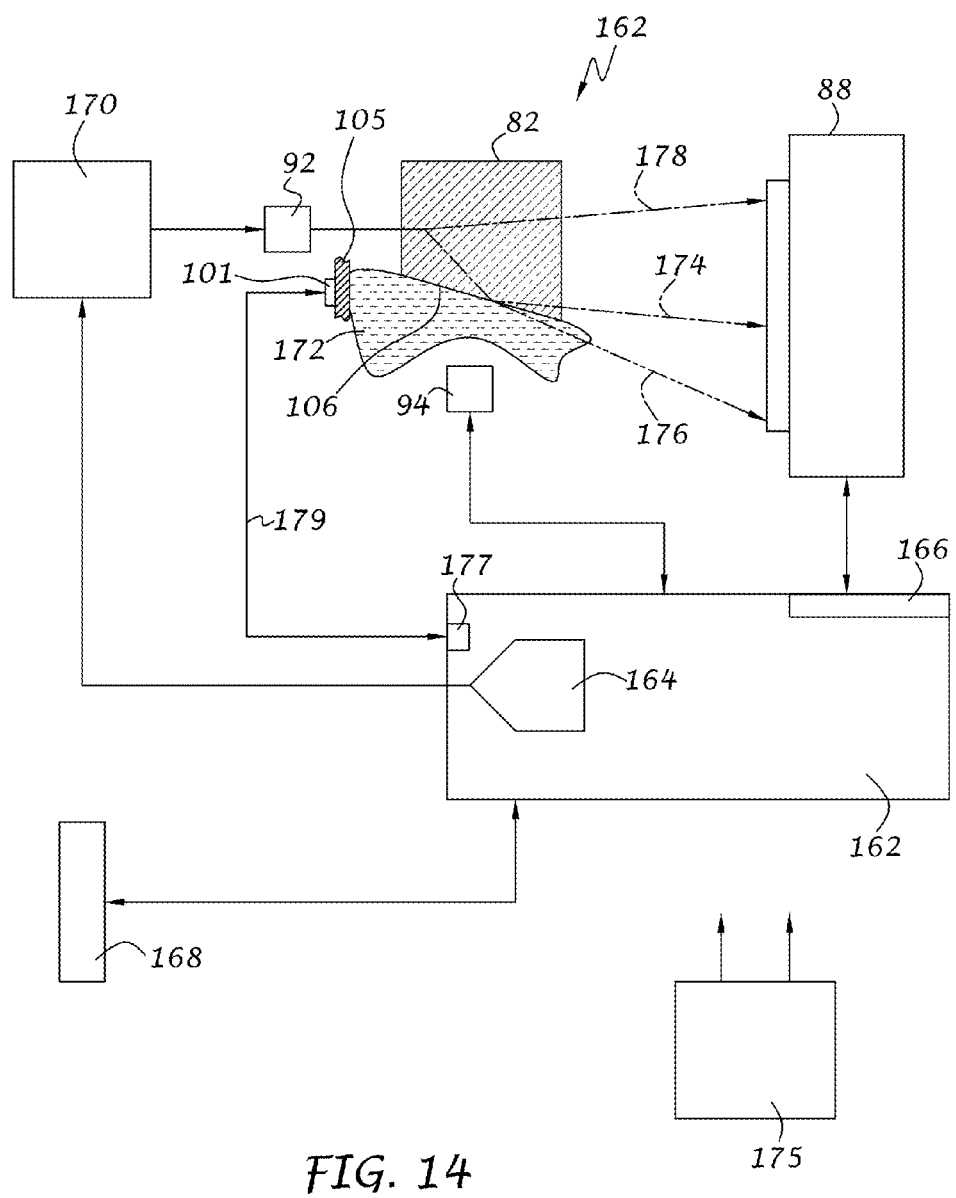
FIG. 14 is an exemplary block diagram of basic electronic, optical, and cleaning module components of the transducer assemblies of the present invention.

As shown in FIG. 14, a block diagram 160 of basic electronic and optical components of the fluid measurement systems of the invention is illustrated. The systems of the invention preferably include a processor 162, such as a microprocessor, with an integrated digital to analog converter (DAC) 164 and an integrated data interface 166 for receiving data from the digital image sensor chip 88. An external interface port 168 is connected to the processor 162 for transferring measurement data, alarm signals, display data, and so on, to a user interface to thereby communicate the quality of the fluid and/or the type of fluid being measured. A current driver 170 for the LED 92 or other light source is connected between the DAC of the processor 162 and the LED 92 for controlling the brightness of the LED under varying atmospheric conditions through a closed-loop feedback system where the LED brightness is monitored by the reference sensor array area 136 (FIG. 16) and optionally temperature data that is received from the temperature sensor 94. In this manner, the LED brightness can be precisely controlled by changing the amount of current flowing through the LED so that a steady brightness of light is directed toward the measuring surface 106, thus contributing to greater accuracy of the fluid measurement system independent of fluid temperature and other atmospheric conditions.

The temperature sensor 94 is connected to the processor 162 for measuring the temperature of the fluid 172 to be measured. The selection of a particular temperature sensor 94 will largely depend on the desired accuracy of the fluid measurement, as temperature can affect the properties of the fluid. Thus, a temperature sensor with relatively high accuracy will result in a fluid measurement of higher accuracy since compensation of the brightness of the light source, and thus the fluid properties, is possible with a more precise temperature reading.

A power source 175 is electrically connected to the processor 162 and other active components, such as the LED 92, sensor 88, and cleaning device 101. The power source can be in the form of one or more batteries or other DC power source, or from an AC power source. For a portable unit used to measure the quality or type of fluid within a tank or container, the fluid measurement system may have one or more replaceable or rechargeable batteries.

The cleaning device 101 is also connected to the processor 162, either directly or indirectly depending on the capabilities of the selected connection port of the processor. Where needed, transducer driving circuitry 177 may be provided as an integral part of the processor 162 or as a separate electrical component or group of electrical components connected between the processor and the cleaning device 101. The driving circuitry 177 can include known electrical components for operating the ultrasonic transduce 101 at a predetermined frequency, different discrete frequencies, and/or sweeping through a range of frequencies, as well as monitoring the performance of the ultrasonic transducer. The driving circuitry 177 is controlled by the processor 162 for operating the cleaning device 101 in accordance with preprogrammed instructions in the processor, memory, or the like, as described above with respect to software implementation.

In accordance with one preferred embodiment of the invention, the processor 162 also receives signals from the cleaning device 101 in a feedback loop (represented by double arrow line 179 in FIG. 14) to automatically adjust operation of the cleaning device based on performance variations under varying environmental conditions, as well changes in fluid properties that may occur under constant fluid flow, intermittent fluid flow, and/or a stagnant fluid condition. In accordance with the invention, the fluid being measured also functions as the cleaning fluid to prevent, substantially reduce, or eliminate film formation on the measuring surface 106 while eliminating the need of disassembly under prior art manual cleaning.

The optical body 82, as previously described, optically interfaces between the LED 92, the fluid 172 being measured, and the digital image sensor chip 88. The measuring surface 106 is in contact with the fluid 172 at a particular cone angle such that some of the light is reflected towards the sensor 88, as represented by arrow 174, while some of the light can be refracted through the fluid 172, as previously described, toward the sensor 88, as represented by arrow 176. Likewise, a calibration portion of the light, as represented by arrow 178, travels through the optical block and towards the sensor 88 to compensate for variations in LED brightness due to temperature and other environmental factors. Although not shown, the bottom surface 108 can be lengthened and the optical sensor module 88 can be shifted to also or alternatively measure absorption characteristics of the fluid, as in the previous embodiment described above.

Figure 15:
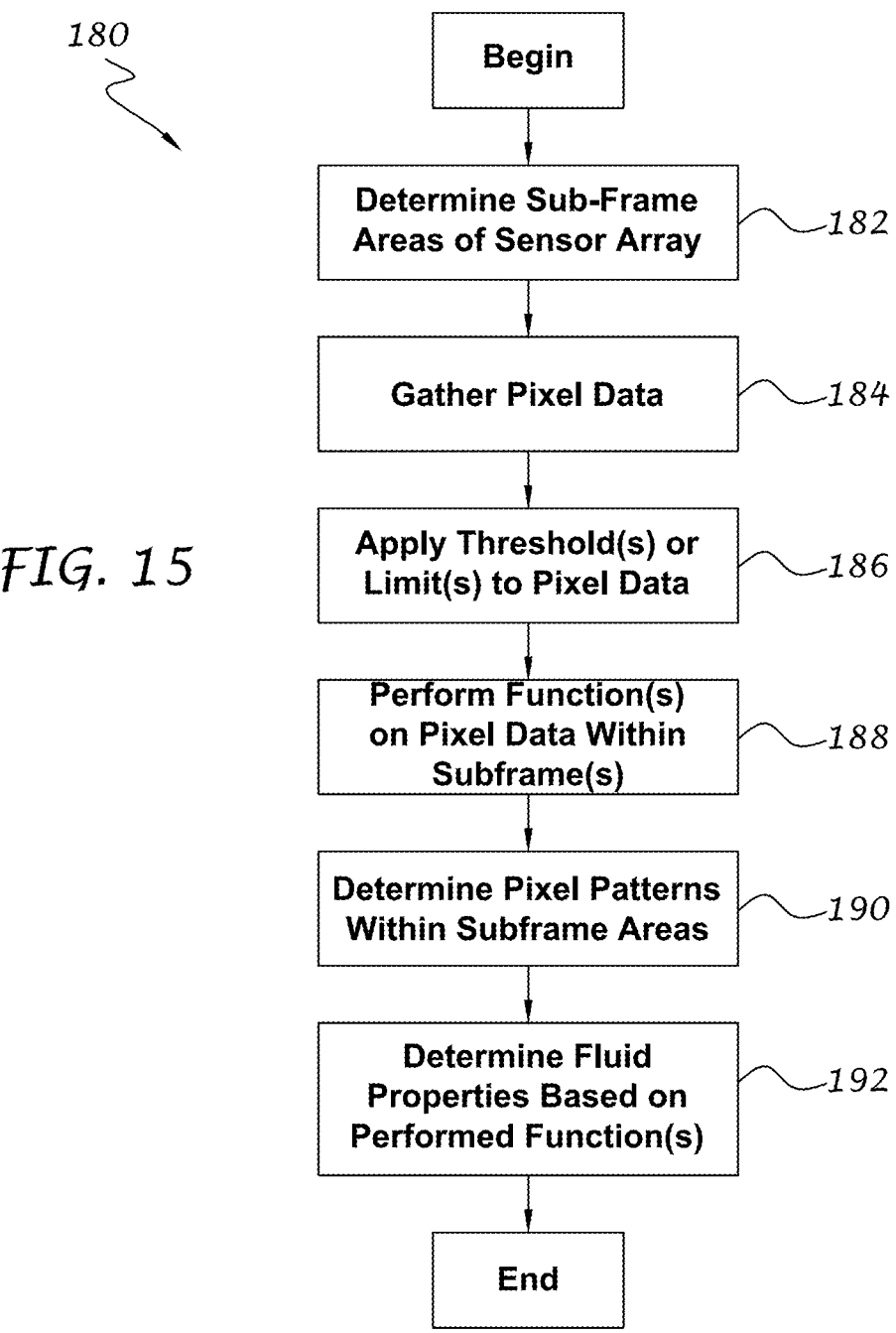
FIG. 15 is an exemplary algorithm for measuring and capturing sensor data related to the measurement systems in accordance with the invention.

Referring now to FIGS. 15 and 16, a method 180 (FIG. 15) for processing data gathered by the optical sensor module 88 is illustrated. The method 180 is similar in some respects to the method 60 previously described, and includes, as shown at block 182, dividing the image area 126 of the optical sensor module 88 into a measurement sensor array area 124 (FIG. 16), a reference sensor array area 136, and a calibration area array 150. As described above, the dark or calibration sensor array area 150 is located between the measurement sensor array area 120 and reference sensor array area 126 but may be eliminated when the optical sensor module 88 has integrated "dark" pixels that are never exposed to radiant energy for calibrating the response of the optical sensor module under varying atmospheric conditions independent of variations in radiant energy.

At block 184 (FIG. 15), the pixel data is gathered. Again, this can be accomplished by gathering pixel data for each line of a frame (image area 126), which can include one or more of the predefined measurement, reference, and calibration areas or portions thereof, the entire area, or a dynamically determined area of the optical sensor module 88. One or more brightness threshold(s) or limit(s) are then applied to the pixel data at block 186 to determine if each pixel is above a predetermined or dynamically determined brightness threshold. For example, in the exemplary embodiment having an optical sensor module in the form of a CMOS color digital image sensor chip with a resolution of 5 megapixels with each pixel capable of distinguishing and capturing 4,096 brightness levels of visible light, the predetermined brightness threshold may be set at level 2,500 for example. It will be understood, of course, that the brightness level threshold for the exemplary embodiment can be set in the range from 1 to 4,096 and may vary, either statically or dynamically, with each sensor array area depending on the particular parameters of the optics and the fluid being measured.

The information gathered from the image area 126 includes pixel brightness and pixel location within each of the predefined reference area 136, measurement area 124, and calibration area 125. At block 188, various functions can be performed on the pixel data including summing pixels above and/or below the predetermined or dynamic threshold, performing a normalization routine between the measurement and reference sensor array areas, and so on. When summing the pixels, the number of pixels above the brightness threshold can be counted, the value of the pixels above the brightness threshold can be added, the number of pixels below the threshold can be added, the value of each pixel below the threshold can be added, and/or the values of the pixels for the entire reference or measurement area can be added without setting the threshold. Other functions can include adding and/or averaging the data from multiple readings of the image area 126, which provides increased magnitude in resolution of the signal strength. At block 190, the shift of data patterns relative to previously gathered or recorded image areas can also be used as an identifier of change in fluid characteristics. Since, according to the exemplary embodiment, each pixel has a brightness magnitude of 4,096 brightness levels, the under/over threshold and over/under limit characteristics can be utilized to include or exclude the data from each pixel within the totals or averages. Accordingly, one or more of the above-described functions can be used to determine one or more fluid properties or characteristics at block 192. A change of one or more fluid properties or characteristics, such as concentration, will cause a corresponding change of signal magnitude as well as a change of pixel signal concentration location within the measurement and reference sensor array areas. Identifying this shift in signal concentration can be utilized to identify additional characteristics of the fluid being measured.

With particular reference now to FIG. 16, an illustration of actual data gathered for a particular concentration of urea in deionized water with the exemplary optical sensor module 88 is shown. The data was imported into a spreadsheet with each cell representing a different pixel. Color values were assigned to each cell according to ranges of brightness within the 4,096 brightness levels. It was found that the pattern in the reference area 136, where the light from the LED is projected directly onto the reference area, remained substantially consistent from frame to frame and for different fluid concentrations.

The measurement area 124 on the other hand changed dramatically even within the small range of urea concentrations of about 30.5% to about 34.5% which, until the present invention, in-line or in-tank DEF quality transducers were only capable of measuring +/−2% concentration from the recommended 32.5% urea concentration. The calibration area 150 also remained constant throughout subsequent frames 126 of the module 88.

As shown in the enlarged portion 190 of the reference area 136, each cell of the spreadsheet is associated with a different brightness level or value. Since the optical sensor module 88 in the exemplary embodiment follows the standardized Bayer pattern with alternating rows 192 and 194 (or columns depending on the module orientation) of green and red pixels and blue and green pixels, respectively. The light source 92 used in the exemplary embodiment was a red LED at a wavelength of approximately 680 nanometers. Thus, for the alternating rows 192 where the green and red pixels are located, the values are generally much higher than the rows where the blue and green pixels are located. Similar results were found for the measurement or "active" area 124 where an enlarged block 196 shows higher values in rows 192 than in rows 194. As shown, the active area 124 is quite distinguishable from the reference area 136 and may vastly change depending on the properties of the fluid being measured.

Likewise, the calibration area 150 with an enlarged block 198 to show the cell details, has values that are substantially lower than the measurement and reference areas since it is in substantially total darkness. As stated earlier, a detected change in these values represents changes in the properties of the optical module 88 independent of radiant energy, which can be used to compensate for measurements of the other areas. For example, an average brightness value of the pixels in the area 150 can simply be subtracted from the average values of the pixels in the measurement and reference areas. Other mathematical or calibration functions can be used without departing from the spirit and scope of the invention.

Figure 17:
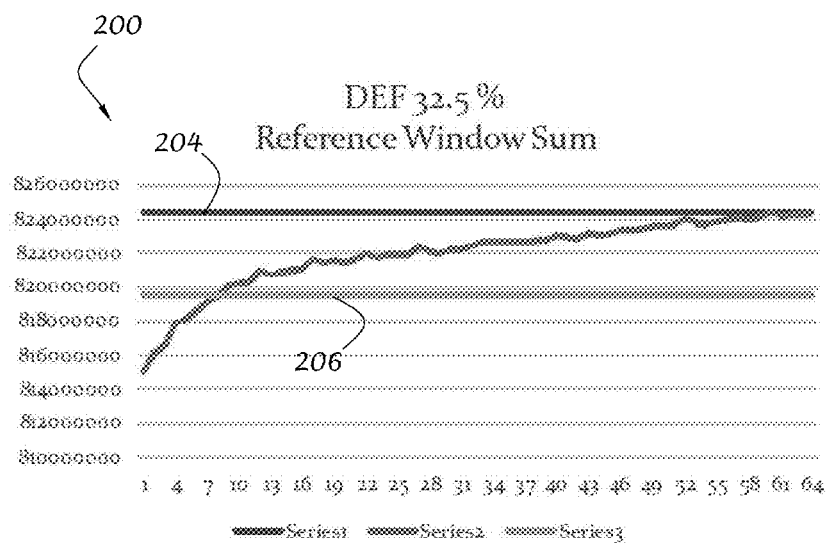
FIG. 17 is a chart plotting a summation of actual reference data of the light source as detected by a reference portion of a digital two-dimensional optical array taken over approximately one hour of time.
Figure 18:
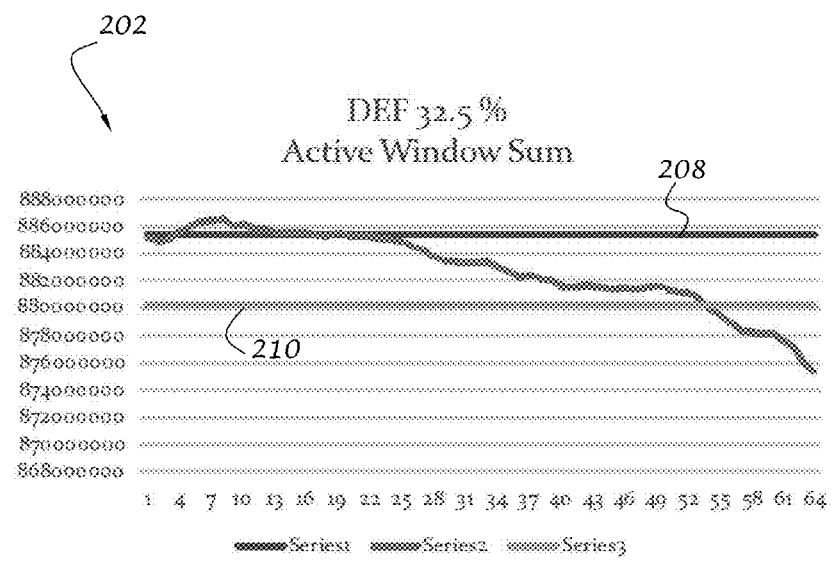
FIG. 18 is a chart plotting the summation of actual measurement data of DEF with a concentration of 32.5% urea in deionized water as detected by a measurement portion of the optical array over the same time interval as FIG. 17.

Referring now to FIGS. 17 and 18, a graph 200 of actual uncompensated data from the reference area 136 and a graph 202 of actual uncompensated data from the measurement area 124 are illustrated for DEF having a urea concentration of 32.5%. Each graph represents values of the brightness level in its associated area plotted over time (approximately one hour) while the DEF was flowing past the measuring surface to determine drift of the fluid in a stationary state. As shown in FIG. 17, an upper limit boundary 204 for the sum of the pixel values of the reference area is located at 824,000,000 and a lower limit boundary 206 thereof is located at 820,000,000. A substantial portion of the brightness in the reference area 136, over the 60-minute period, stayed within the upper and lower boundaries. The drift may be attributed to separation of the fluid components while the fluid is stationary, i.e. not flowing across the optics, and/or the commencement of film build-up on the measuring surface of the optical body, since the cleaning device 101 was not present during these tests. Likewise, as shown in FIG. 18, an upper limit boundary 208 for the sum of the pixel values in the measurement area is located at a value of 886,000,000 and a lower limit boundary 210 is located at a value of 880,000,000. A substantial portion of the average brightness in the reference area 136, once stabilized, over the 60-minute period, stayed within the upper and lower boundaries.

Figure 19:
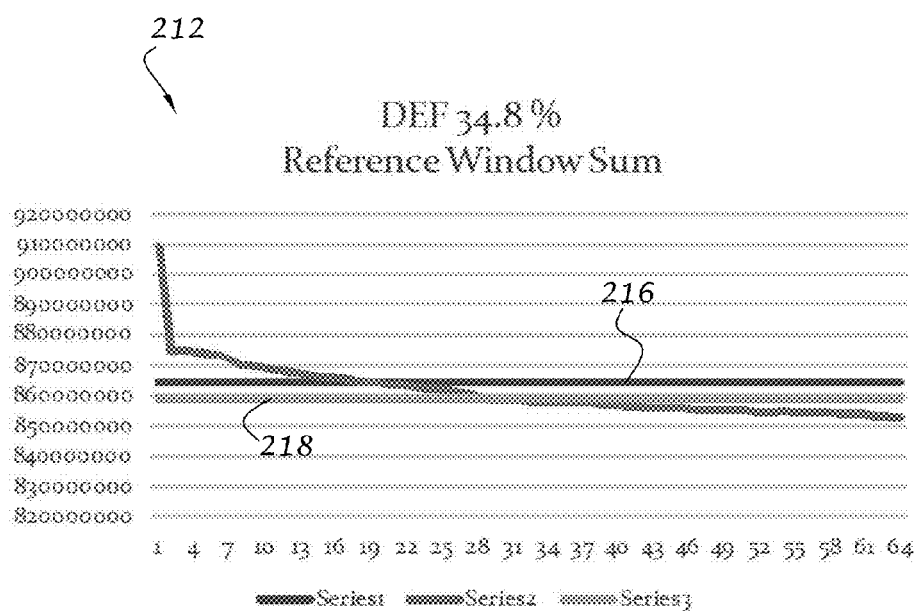
FIG. 19 is a chart plotting the summation of actual reference data of the light source under different measurement circumstances than FIG. 17, as detected by a reference portion of a digital two-dimensional optical array taken over approximately one hour of time.
Figure 20:
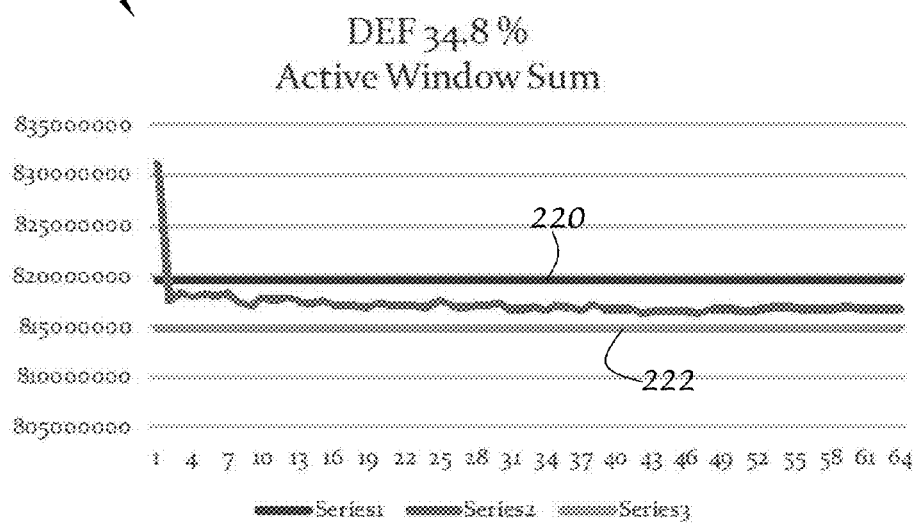
FIG. 20 is a chart plotting the summation of actual measurement data of DEF with a concentration of 34.8% urea in deionized water as detected by a measurement portion of the optical array over the same time interval as FIG. 17.
Figure 21:
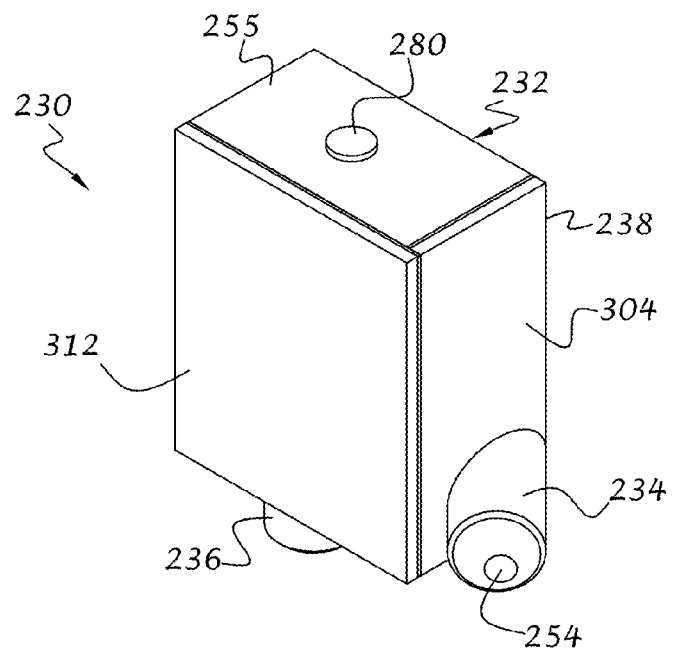
FIG. 21 is a rear isometric view of an exemplary measurement transducer assembly in accordance with a further embodiment of the invention incorporating an optical sensor array, impedance measurement assembly, and cleaning module for minimizing or eliminating contamination on measuring surfaces that may affect the measurements.
Figure 22:
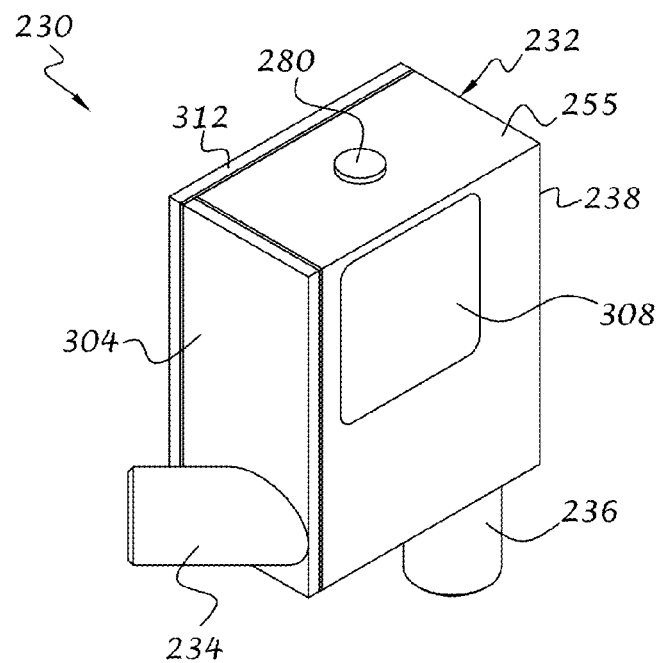
FIG. 22 is a front isometric view thereof.

Referring now to FIGS. 19 and 20, a graph 212 of actual uncompensated data from the reference area 136 and a graph 214 of actual uncompensated data from the measurement area 124 are illustrated for DEF having a urea concentration of 34.8%. Each graph represents an average value of the brightness level in its associated area plotted over time (approximately one hour) to determine drift of the fluid in a stationary state. As shown in FIG. 19, an upper limit boundary 216 for the sum of the pixel values of the reference area is located at 860,000,000 And a lower limit boundary 218 thereof is located at about 865,000,000. A substantial portion of the average brightness in the reference area 136, over the 60-minute period, stayed within the upper and lower boundaries. Again, the drift can be attributed to separation of the fluid components and/or film buildup on the measuring surface. Likewise, as shown in FIG. 18, an upper limit boundary 220 for the sum of the pixel values in the measurement area is located at a value of 820,000,000 and a lower limit boundary 222 is located at a value of 815,000,000. A substantial portion of the average brightness in the reference area 136, once stabilized, over the 60-minute period, stayed within the upper and lower boundaries.

Due the very narrow band range of the measured DEF concentrations above, a very high degree of accuracy for determining the concentration of urea in DEF has been obtained. It has been calculated that the accuracy of the percent urea in deionized water can be determined at least within +/−0.002% or even greater accuracy, especially with the addition of the cleaning device 101 to ensure a measuring surface virtually free of contaminants during long measurement runs, as would be anticipated in the transportation industry where it would not be practical to clean the measuring surface after each acquired measurement in a SCR system. Accordingly, the present invention is a substantial improvement over prior art systems that have an accuracy of +/−2%, and yet can remain competitive in cost.

The greatly increased accuracy in DEF concentration determination is especially advantageous for example in SCR systems where, even if the urea concentration of the DEF is not ideal, the DEF can be accurately metered into the SCR system based on feedback from the NOx sensor and the DEF concentration as measured by the present invention to thereby maximize the reduction of NOx emissions in practically real time while allowing wide variations in DEF concentrations.

It will be understood that measurement of the DEF and the particular results obtained are by way of example only, since it is anticipated that substantially any fluid (including but not limited to gases, liquids, and solutions) and solid materials can be measured through the systems and methods of the present invention.

It will be further understood that the invention can include different calibration and/or measurement techniques. In accordance with a further embodiment of the invention, the reference area may be eliminated and a substantial portion of the image area 126 can be used alternatively for measuring fluid parameters and variations in light and surface contaminants. This can take place by filling the space surrounding the measuring surface 106 of the optical body 82, taking a first reading in the image area, then emptying the space surrounding the measuring surface and taking a second reading in the image area. The second reading can then be subtracted from the first reading or the first and second readings may be used in a normalization routine to eliminate error caused by variations in LED intensity and surface contaminants. An exemplary normalization routine can include the following formula:

$$(A-B)/(A+B)$$

Where "A" represents the reading of the image area when the space is empty and "B" represents the reading of the image area when the space is full of liquid. In this manner, signal variations associated with environmental conditions will be part of the numerator and denominator, and thus cancel out. The above formula can also be used for normalizing the reading between separate measurement and reference areas of the optical sensor module.

Referring now to FIGS. 21-24, a system 230 for measuring fluid properties, including fluid composition and quality for example, as well as other parameters, in accordance with yet another preferred embodiment of the invention is illustrated. The system 230 preferably includes multiple internal measuring surfaces for determining different fluid properties, including optic and impedance measuring surfaces that come in direct contact with the fluid. The system 230 ensures that the measuring surfaces will be free of foreign material that may skew the fluid measurement readings and thus lead to incorrect determination of the fluid properties.

Although the system 230 will be described in the context of optical and impedance measuring surfaces to facilitate description of the invention, it will be understood that the invention is not limited thereto, as the structure and methods disclosed herein may be applied to any measuring surface that may come in contact with the fluid being measured using virtually any measurement technology, so that accumulation of foreign material on such surfaces is prevented, substantially reduced, or eliminated. Such surfaces may include, but are not limited to, optical lenses, filters, prisms, conduits, plates, and so on, related to optical fluid measurement, liquid level detection, and so on; capacitive electrodes for determining liquid level and/or fluid properties, tuning fork surfaces for determining liquid level and/or fluid properties, resistance wires, plates, and coils used in liquid level measurement, and so on.

The system 230 can be configured for inline, in-tank, or in-tank-head measurement systems to thereby measure the quality and/or type of a fluid as it is being transferred from one location to another, such as for example from a DEF tank to a catalytic converter or other part of a SCR system; from a filling station to the DEF tank; from the DEF tank and back into the DEF tank, and so on. A suitable in-tank-head approach that both determines the quality of fluid as it is withdrawn from a tank and the level of that same fluid within the tank is disclosed in U.S. application Ser. No. 14/677,914 filed on Apr. 2, 2015, the disclosure of which is hereby incorporated by reference. To that end, the cleaning system and method as disclosed herein can be employed for cleaning the optical measuring surfaces, impedance measuring surfaces, and liquid level measuring surfaces by having one or more cleaning devices, such as the ultrasonic transducers previously described, strategically placed at one or more locations so that cavitation bubbles are created in the liquid to generate cleaning action on measurement surfaces contacting the liquid.

The system 230 includes a housing 232 with a first connector 234 and a second connector 236 extending therefrom for receiving tubing or the like to transport the fluid to be measured through the housing 232 and across the various measuring surfaces located within the housing, as will be described below. The first and second connectors 234, 236 can serve either as fluid input or fluid output conduits with respect to the housing 232.

Figure 23:
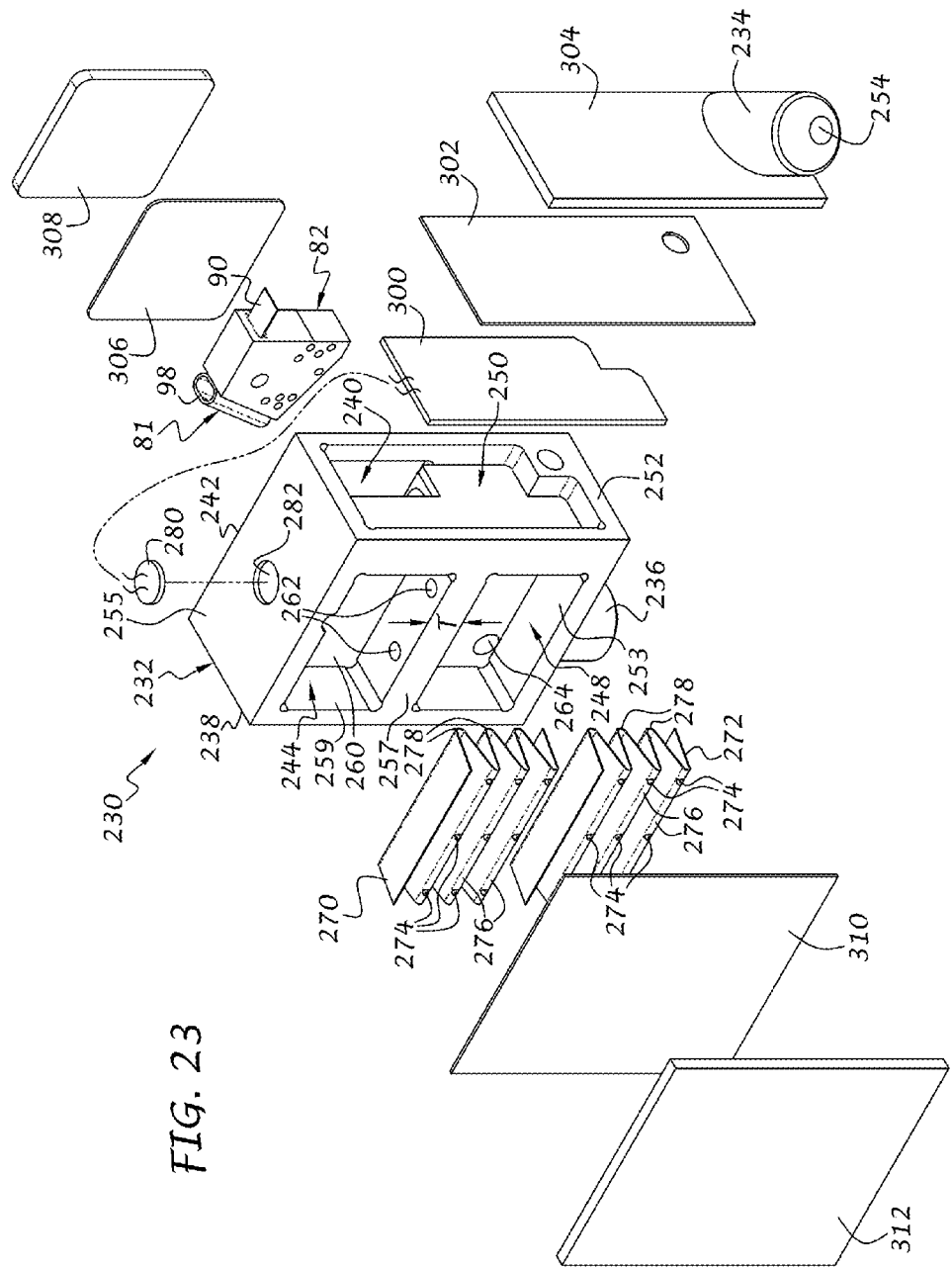
FIG. 23 is a rear exploded isometric view thereof.
Figure 24:
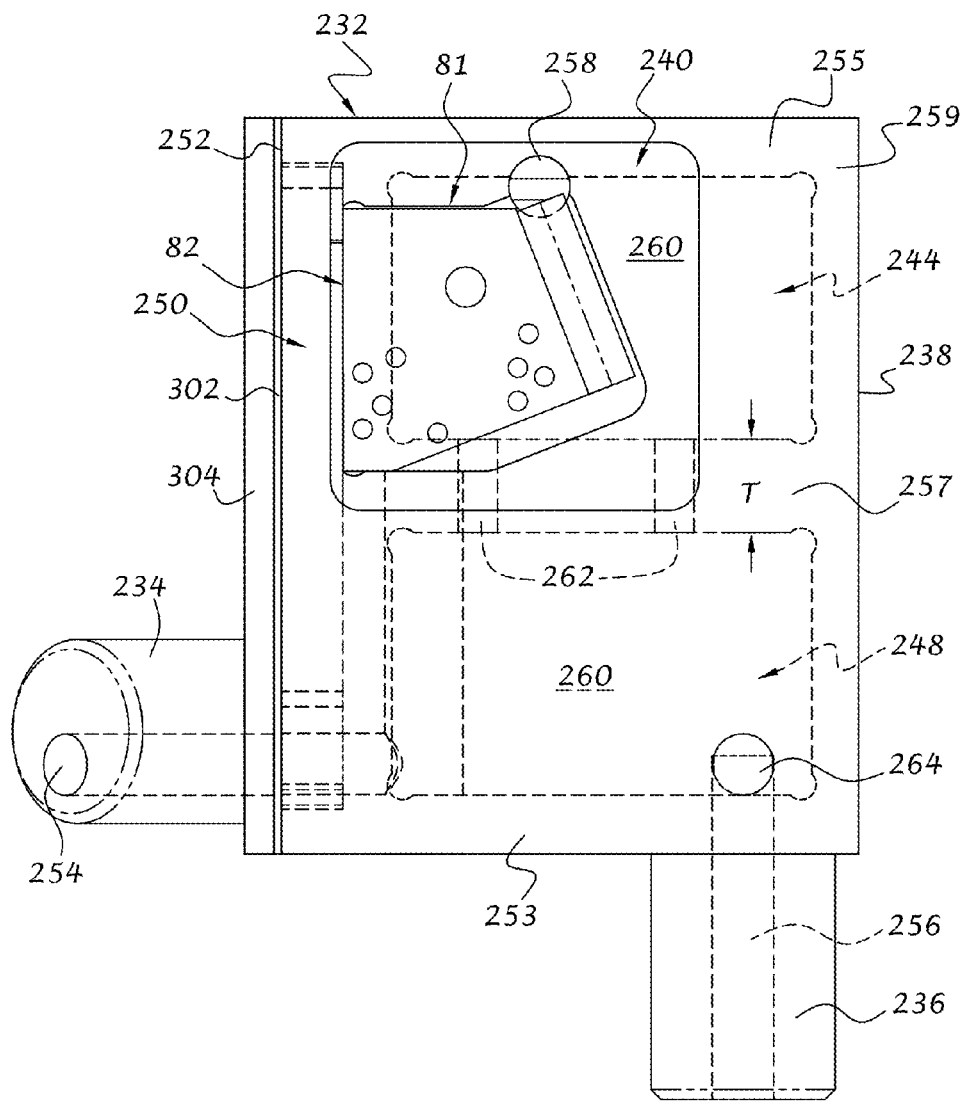
FIG. 24 is a front elevational view of a housing that forms part of the measurement transducer of FIG. 21 and showing hidden features of the housing in dashed line.

As best shown in FIGS. 23 and 24, the housing 232 includes a first compartment 240 formed in a front wall 242 thereof for receiving an optical measurement assembly 81 (previously described), a second compartment 244 formed in a rear wall 246 of the housing 238, a third compartment 248 formed in the rear wall 246 below the second compartment 244, and a fourth compartment 250 formed in a side wall 252 of the housing 232. The first compartment 240 is in fluid communication with the first connector 234 via a first conduit 254 formed therein while the third compartment 248 is in fluid communication with the second connector 236 via a second conduit 256 formed therein. The first compartment 240 and second and third compartments 244, 248 are separated by a first internal wall 260 that extends between a lower wall 253 and an upper wall 255 of the housing 232. Likewise, the second and third compartments 244, 248 are separated from each other by a second internal wall 257 that extends between the side wall 252 and an opposite side wall 259 of the housing 232. The first and second compartments 240, 244 are in fluid communication with each other via a first bore 258 that extends through the first internal wall 260. Likewise, the second and third compartments 244, 248 are in fluid communication with each other via one or more restricted flow components 262, embodied as a pair of second bores that extend through the second internal wall 257 between the second and third compartments. Finally, the third compartment 248 is in fluid communication with the second conduit 256 via a third bore 264 that extends through the first internal wall 260 at a location spaced from the first compartment 240. In this manner, the fluid to be measured can continuously flow through and fill the first, second, and third compartments for measuring the fluid properties before exiting the housing 232. Once the fluid is measured, it exits the housing and can be directed to a tank that holds the fluid, a catalytic converter in a SCR system, or other system or component(s) of the vehicle or machine that utilizes the fluid.

The first compartment 240 is configured to receive an optical measurement assembly 81 for optically monitoring the properties of the fluid in the housing 238, as previously described, which incorporates the first signal generating device in the form of an optical array. The second and third compartments 244 and 248 are configured to receive electrodes 270 and 272, respectively, which form part of a second signal generating device for measuring the impedance of the fluid. The second intermediate wall 257 has a thickness "T" that defines the spacing or distance between the electrodes 270 and 272. The one or more restricted flow components 262 are of a particular diameter or cross dimension and the length of the restricted flow components 262 as defined by the wall thickness T, establish a restricted flow space or volume through which the fluid, and thus the electrons associated with the fluid, must travel between the electrodes 270 and 272. It will be understood that the restricted flow components 262 can include a single bore or more than two bores, and can be of any suitable shape, size, and length depending on the fluid and the fluid properties to be measured.

As best shown in FIG. 23, each of the electrodes 270 and 272 include a conductive plate with holes 274 formed therein to allow fluid in the compartments 244, 248 to flow through the electrodes and expose opposing surfaces of the electrodes so that the fluid within the compartments 244, 248 can flow through the electrodes to thereby maximize the surface area of the electrodes in a minimum amount of space. To that end, each electrode 270, 272 can be shaped to maximize surface area. By way of example, each plate can be formed with parallel, alternating ridges 276 and valleys 278 to enable more electrode material, and thus surface area, to fit within the compartments 244, 248. It will be understood that the electrodes can be formed of any suitable shape and size.

Each conductive plate is preferably coated with an electrically non-conductive layer (not shown) on opposing sides thereof and through the holes 276 so that the conductive plate is isolated from the liquid within the compartments. In this manner, corrosion of the electrodes as well as their consequent electrical signal degradation are substantially reduced or eliminated. Insulative materials that may be suitable for the non-conductive layer can include, but are not limited to, Parylene, fluoropolymers, plastics, elastomers, enamels, ceramics, and so on, and that such materials may be applied using different techniques, such as painting, powder coating, dipping, vapor deposition, and so on, in different thicknesses depending on the particular liquid to be measured.

Moreover, some non-conductive materials may be more suitable then others for certain liquids to be measured. For automotive-type liquids, including DEF, antifreeze, windshield washer fluid, oil, and the like, it has been found that a thin coating, such as 0.5 to 1 Mil thickness of Parylene™ or other chemical vapor deposited poly(p-xylylene) polymers, is an especially suitable insulative layer for the liquid quality measurements that will be described in greater detail below. However, it will be understood that other materials and/or material thickness can be used for the insulative layers without departing from the spirit and scope of the invention.

It will be further understood that in some instances the insulative layers may be eliminated, such as when the liquid is substantially non-conductive or when the electrodes are operatively associated with other components, such as a sacrificial anode, that is intended to bear the brunt of any potential galvanic corrosion, thereby reducing or eliminating degradation of the electrodes and thus subsequent degradation in the measurement of the liquid under consideration.

In accordance with a further embodiment of the invention, the insulative layers, when used, can be partially conductive, e.g. the layers need not be a perfect insulator, depending on the measuring techniques used for determining fluid properties.

Due to the configuration of the insulated plates, their relative position, and the fluid flow therebetween, a series RC network is created that minimizes plate capacitance and maximizes measurement of impedance through the fluid. Using a large area capacitive plate to provide non-electrical contact with the fluid causes an additional RC network, or impedance to be interjected, while minimizing the RC network of the plates and insulative coating. As the plate size is increased, so is the effective cross section of the fluid. Thus, the ratio of the capacitors (plate insulation and fluid capacitance) is relatively constant. In order to maximize accuracy of the fluid measurement, the effect of plate capacitance is minimized by increasing the spacing between the plates to lower the fluid dielectric constant, as well as creating the restricted flow components 262 to reduce the cross section of the fluid. Where space constraints between the plates become a concern, it is possible to achieve similar results by further restricting fluid flow between the plates. Hence, the restricted flow components can vary in size and number to accommodate a particular plate configuration. Accordingly, accuracy of the impedance measurement of the fluid is greatly increased and the system of the invention is capable of differentiating different fluids in a mixture of fluids with relatively high accuracy.

However, even with the accuracy greatly increased over prior art impedance measurement techniques, there still remains the possibility that contaminants, films, particles, or any other undesirable material, will collect on the measuring surfaces of the electrodes, and change the plate impedance, which may have an undesirable effect on measuring the impedance of the fluid. In many real-world scenarios, it is impractical to remove the plates for cleaning due to the inaccessibility of the electrodes. Even when the electrodes are accessible, the service intervals to clean the measuring surfaces of the electrodes may be impractical. It has been observed that contaminants may almost immediately begin to collect on the electrodes and fluid measurements can quickly become skewed. Accordingly, the potentially high accuracy of the impedance measurements of the invention can be affected over varying amounts of time without a way to continuously or intermittently clean the measuring surfaces. The same holds true for the optical measuring surface of the optical measurement assembly 81 (FIG. 23) previously described.

Therefore, in accordance with the invention, and as shown in FIG. 3, a cleaning device 280 is positioned within a depression 282 formed in the upper wall 255 of the housing 238 at one or more locations and/or orientations with respect to the housing. The cleaning device 280 may additionally or alternately be positioned on other wall surfaces without departing from the spirit and scope of the invention. Although the wall 255 is shown as integral with the housing 238, the wall can comprise a sheet of suitable material mounted over an opening in the housing and to which the cleaning device 280 is attached. The cleaning device 280 is similar in construction to the cleaning device 101 and cleaning device 25 and generates ultrasonic waves in the fluid being measured for cleaning the measuring surface of the optical body 82 and the measuring surfaces of the electrodes 270 and 272, as well as other surfaces on which contaminants may collect, under the principles as previously described. The transducer 280 can be constructed of piezoelectric or magnetostrictive materials that vibrate at a predetermined frequency, discrete frequency steps, and/or sweeping frequencies in the ultrasonic bandwidth.

In use, the one or more transducers placed at one or more locations on or in the housing 238 and/or other locations where the fluid is subjected to ultrasonic vibration so that particles, contaminants, film, layers, and the like that may tend to collect on, or be in the process of collecting on, the measuring surfaces can be cleaned ultrasonically during fluid flow, when the fluid is stopped, or at any other convenient time for cleaning or ensuring the cleanliness of the measuring surfaces. It will be understood that other cleaning devices can be used without departing from the spirit and scope of the invention. As in the previous embodiments, the fluid being measured also functions as the cleaning fluid to prevent, substantially reduce, or eliminate film formation on the measuring surfaces.

During the cleaning operation, fluid properties can continue to be monitored. Detecting differences in fluid properties at the commencement of the cleaning operation would suggest that the cleaning is effective, while stabilization of the fluid properties at some point after commencement of the cleaning process would suggest that cleaning of the measuring surfaces has completed.

In accordance with a further embodiment of the invention, a separate reservoir of cleaning fluid (not shown) can be provided. In this instance, when the cleaning operation is commenced, the flow of fluid being measured would be terminated and the flow of cleaning fluid would commence to flush out contaminants while operating the cleaning device 280. When the cleaning operation has finished, the flow of fluid being measured would then recommence and the flow of cleaning fluid would be terminated.

The system 230 for measuring fluid properties also includes a printed circuit board (PCB) 300 positioned in the fourth compartment 250 of the housing 238, followed by a side gasket 302 and a side cover 304, which is in turn connected to or integrally formed with the connector 234, to seal the PCB within the housing and isolate it from the fluid flow through the housing. The PCB is similar in construction to the PCB previously described, with the exception that interface circuitry (not shown) for injecting a frequency or series of frequencies, and/or an electrical pulse at one or more amplitudes across the electrodes via processor control, as well as appropriate circuitry for measuring the impedance of the fluid between the electrodes in response to the injected frequencies and/or electrical pulse(s), can be associated with the PCB and/or the controller. The provision of the side cover 304 facilitates access to the PCB for installation, servicing, or replacement.

The optical measurement assembly 81 is positioned in the second compartment 240, followed by a front gasket 306 and a front cover 208 to seal the optic within the housing. The provision of the front cover 208 and gasket 306 facilitates installation and removal of the optical measurement assembly 81 with respect to the housing 238.

A rear gasket 310 followed by a rear cover 312 is connected to the housing 238 and covers the compartments 244 and 248, and the electrodes located therein. Again, the provision of the rear cover 312 permits access to the compartments 244 and 248 for installation, removal, or service of the electrodes 270 and 272.

Figure 25:
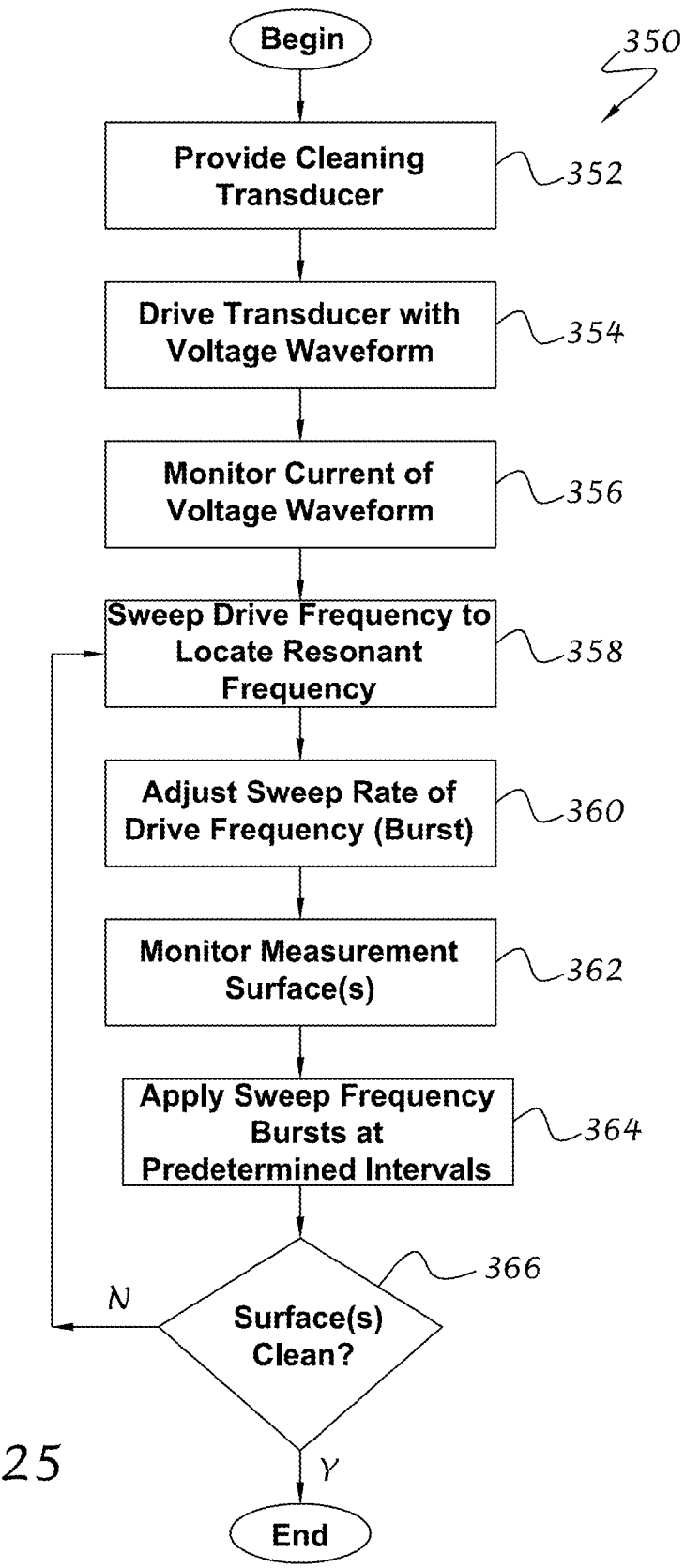
FIG. 25 is a flow chart illustrating a method of cleaning the measuring surface(s) during operation of the transducer assemblies for minimizing or eliminating contamination that may collect on the surfaces to thereby obtain repeatable fluid measurements.

Referring now to FIG. 25, a method 350 for cleaning measuring surfaces of fluid measuring devices is illustrated. The prior art practice of cleaning measuring surfaces at service intervals of a vehicle or other equipment, is both time consuming and costly in terms of the vehicle or equipment being in an inoperable state during the cleaning, as well as the cost of labor to disassemble the apparatus, removing and cleaning the measuring unit, then installing the measuring unit and reassembling the apparatus. The method 350 of the present invention is especially advantageous since the measuring surfaces can be cleaned at any time, either constantly or intermittently, as often as needed or determined in order to ensure accurate measurement readings of fluid properties or fluid quality that are free from contaminant buildup on the measuring surfaces.

The method 350 includes affixing a cleaning device, such as an ultrasonic transducer as previously described, to the wall of the housing containing the measuring surfaces or at other suitable location(s), as denoted at block 352. The housing or the portion of the housing or other location to which the transducer is affixed is constructed of a material compatible with the fluid being measured and compatible with vibrations of the ultrasonic transducer. The location at which the transducer is affixed preferably has a thickness of approximately one-quarter wavelength of the ultrasonic transducer driving frequency. This wavelength is a function of the sound propagation of the specific material and the resonant frequency of the ultrasonic transducer. Suitable materials for the housing portion can include, but are not limited to, PEEK, acrylic, metals, ceramics, or other materials with adequate sound propagation, where at least a substantial portion of the vibration generated by the ultrasonic transducer is not absorbed by the material.

At block 354, the transducer is driven by a voltage wave form at a selected frequency. Preferably, the voltage wave form is a differential square wave ranging from about one volt to about 50 volts, and more preferably between about 12 volts and 30 volts. At block 356, the current of the voltage wave form is monitored to determine whether the ultrasonic transducer reaches resonance. Since a significant amount of power is dissipated when driving the transducer, the duration of the driving waveform must be limited to avoid heating of the fluid being measured within the housing. Many materials and fluids change properties with an increase in temperature, such as the refractive index and impedance of fluids as previously described, so it is preferred that heating of the fluid be minimized during cleaning. However, it will be understood that where the fluid properties are not being measured during the cleaning operation, heating of the fluid may be acceptable to a certain degree, depending of course on the type of fluid under consideration. Moreover, when separate cleaning fluid is injected into the housing for the sole purpose of cleaning the measuring surfaces, fluid heating may become even less critical.

During the cleaning operation, the resonant frequency of the ultrasonic transducer typically shifts to a higher frequency under load than when it is initially driven, which can affect transducer operation and whether or not the measuring surfaces will be cleaned. This is especially important when the cleaning solution is the fluid being measured. For water-based fluids, such as DEF in SCR systems as previously described, control of the cleaning process becomes even more difficult.

Although there are challenges in using the fluid under measurement as the cleaning solution, there are several advantages in so doing in accordance with the invention. By eliminating the separate introduction of cleaning fluids only for the purpose of cleaning, and thus the extra components and costs associated with maintaining a separate cleaning solution tank with the controls to stop and start flow of the fluid under measurement and start and stop flow of the cleaning solution into the measurement housing, removing the cleaning solution from the measurement housing and reintroducing the fluid under measurement into the housing, and so on. Using the fluid under measurement as the cleaning solution also allows the vehicle or machine to continue operating during the cleaning process rather than the attendant down time that would occur when cleaning solutions may be introduced that are not compatible with the SCR system or other components of the vehicle or machine. However, it will be understood that, although disadvantageous, a further embodiment of the present invention includes the introduction of a separate cleaning solution into the measurement housing, it being understood that the capability of in situ cleaning of the measuring surfaces without the necessity of disassembling the system with its attendant costs and downtime of the vehicle or machine associated with the fluid under measurement is a particular advantageous feature of the invention.

In order to effectively use the fluid under measurement as the cleaning solution, the driving frequency is shifted to track the resonant frequency shift of the transducer under load (block 358) by driving the transducer with a sweeping frequency that commences slightly lower than the initial resonant frequency of the transducer to a slightly higher frequency than the resonant frequency of the transducer under load. The resonant frequency may change due to a difference in material properties due to ambient temperature fluctuations, differences in fluid properties as the fluid flows through the system, and perhaps for other reasons. Advantageously, no matter what the reason for the resonant frequency shift, this sweeping action automatically picks up the higher frequency of the transducer under load for effective generation of micro cavitation bubbles in the fluid and thus the effective cleaning action of the measuring surfaces, as well as other surfaces that may be in the vicinity and in contact with the fluid.

At block 360, the sweep rate or "burst" of the applied driving frequency is adjusted to prevent excessive dwell time of the transducer, and thus excessive power dissipation and subsequent heating of the surrounding area.

At block 362, the sweep frequency burst is repeated a predetermined number of times during a first time period, for example several sweep frequency bursts over several seconds, in order to provide intermittent or continuous agitation of the fluid for efficient cleaning action of the measuring surfaces.

At block 364, the measuring surfaces of the fluid measuring system are monitored to determine if an abnormal or predetermined increased rate of change of fluid properties over time is occurring, indicative of an effective cleaning operation.

At block 366, it is determined whether or not the fluid properties continue to change at a rate commensurate with a surface cleaning operation. If the commensurate rate of change falls outside of the predetermined range after a predetermined time period, e.g. an abnormal rate of change in fluid property is no longer detected so that the fluid properties have stabilized, it is determined that the cleaning operation has been successful and the transducer can be deactivated for a predetermined time. The plurality of driving frequency bursts during the first time period can then be repeated automatically at predetermined intervals. It was found that effective cleaning of measuring surfaces during fluid flow was achieved by applying several multiple-second bursts of repeated sweeps. Long term maintenance cleaning can be achieved with the present invention by applying a burst of sweeps every few minutes during the operational time of the measurement system.

It will be understood that the sweep frequencies, number of bursts, frequency of bursts, as well as the driving voltage wave form and range of driving voltages can greatly vary without departing form the spirit and scope of the invention. It will be further understood that the cleaning operation can continue at predetermined intervals without monitoring the cleaning surface(s) or the fluids for abnormal changes in fluid properties and/or changes in fluid properties at predetermined rates.

Accordingly, the present invention provides a system and method for determining the properties of fluids and other parameters with a higher degree of accuracy than prior art systems in order to quantify whether or not proper fluid and/or the proper concentrations of fluids are being used in vehicles, machinery, and so on, while dynamically and automatically cleaning the measuring surfaces associated with such systems, thereby reducing or eliminating the collection of contaminants at least on measuring surfaces of the system, thus leading to more consistent and accurate fluid property measurements.

It will be understood that the method of cleaning measuring surfaces in accordance with the invention is not limited to the fluid measuring systems described herein, but may be used with any measuring system where contaminants or foreign material may collect on one or more measuring surfaces of the measuring system.

It will be understood that the above-described embodiments can be permanently mounted on equipment or may be constructed as portable units for measuring the properties of a variety of different fluids within transport lines, tanks or containers, across many industries, by users, field technicians, maintenance workers, claims adjusters, and so on.

It will be understood that terms of orientation and/or position as used throughout the invention relate to relative rather than absolute orientations and/or positions.

It will be appreciated by those skilled in the art that changes could be made to the embodiments described above without departing from the broad inventive concept thereof. It will be understood, therefore, that this invention is not limited to the particular embodiments disclosed, but it is intended to cover modifications within the spirit and scope of the present invention as defined by the appended claims.

What is claimed is:

1. A first system for determining at least one property of a fluid for assessing a suitability of the fluid for use in a second system different from the first system, the first system comprising:
a housing for receiving the fluid;
at least one measuring surface located in the housing and configured for contacting the fluid;
a signal generating device associated with the at least one measuring surface for generating signals related to the at least one property of the fluid for assessing the suitability of the fluid for use in the second system; and
a cleaning device comprising a transducer operably associated with the housing, the transducer being operable with application of a voltage wave form at a driving frequency for generating micro cavitation bubbles that are transmitted through the fluid and toward the at least one measuring surface to thereby remove undesirable material from the at least one measuring surface;
wherein the fluid is: 1) normally used in the second system; 2) measured via the at least one measuring surface and the associated signal generating device of the first system for determining the at least one property of the fluid and thus the suitability of the fluid for use in the second system; and 3) used as a cleaning fluid by the transducer in the first system to clean the at least one measuring surface to accurately determine the at least one property of the fluid.

2. A first system according to claim 1, and further comprising a processor for receiving signals from the signal generating device and determining the at least one property of the fluid.

3. A system according to claim 2, wherein the processor is operable to monitor a current of the voltage wave form that drives the transducer to determine when the transducer reaches at least one of first and second resonant frequencies to thereby control operation of the cleaning device.

4. A first system according to claim 3, wherein the transducer comprises an ultrasonic transducer connected to a wall of the housing in close proximity to the at least one measuring surface, with the fluid located between the wall of the housing and the at least one measuring surface.

5. A system according to claim 1, wherein the housing has a fluid input conduit and a fluid output conduit, and further wherein the fluid constantly flows into the housing through the fluid input conduit, through the housing along the at least one measurement surface during cleaning of the at least one measuring surface, and during determining of the at least one fluid property, and exits the housing through the fluid output conduit.

6. A system for determining at least one property of a fluid for assessing a suitability of the fluid for use in a second system, the first system comprising:
a housing for receiving the fluid;
at least one measuring surface located in the housing and configured for contacting the fluid;
a signal generating device associated with the at least one measuring surface for generating signals related to the at least one property of the fluid;
a processor operably connected to the signal generating device for receiving signals therefrom and determining the at least one property of the fluid;
an ultrasonic transducer connected to a wall of the housing, the ultrasonic transducer being operably connected to the processor for both monitoring the transducer and controlling operation of the transducer based on the monitoring, with a high frequency voltage waveform applied to the transducer that in turn vibrates the housing wall and produces micro cavitation bubbles in the fluid directed toward the at least one measuring surface to thereby remove undesirable material from the at least one measuring surface upon collapse of the bubbles; and
wherein the ultrasonic transducer operates at a first resonant frequency and a second resonant frequency different from the first resonant frequency under an applied load, the processor being operable to 1) drive the transducer with voltage wave forms at driving frequencies, and 2) monitor the transducer to determine when the transducer reaches at least one of first and second resonant frequencies to thereby drive the transducer with a driving frequency commensurate with the at least one first and second resonant frequencies for effective cleaning of the at least one measuring surface.

7. A system according to claim 6, wherein the ultrasonic transducer is driven by the processor with the voltage wave forms over a sweeping range of driving frequencies encompassing the first and second resonant frequencies; with the processor monitoring a current of the voltage wave form to determine when the transducer reaches the second resonant frequency to thereby locate and effectively utilize the second resonant frequency for effective cleaning of the at least one measuring surface.

8. A system according to claim 7, wherein the processor is configured to drive the ultrasonic transducer over the sweeping range of driving frequencies over a first period of time to create a single burst of swept frequencies.

9. A system according to claim 8, wherein the processor is configured to repeat the single bursts of swept frequencies at discrete time intervals over a second period of time to thereby provide intermittent or continuous micro cavitation bubbles in the fluid directed toward the at least one measuring surface to thereby remove undesirable material from the at least one measuring surface upon collapse of the bubbles in the fluid for effective cleaning of the at least one measuring surface.

10. A system according to claim 9, wherein the processor is configured to monitor the at least one measuring surface via the signal generating device to determine whether a predetermined rate of change of the at least one fluid property over time is occurring to thereby quantify an effectiveness of the cleaning of the at least one measuring surface.

11. A system according to claim 10, wherein the processor is configured to monitor when the at least one measuring surface has achieved maximum cleanliness by determining that the predetermined rate of change of the at least one fluid property is no longer present.

12. A system for determining at least one property of a fluid, the system comprising:
a housing for receiving the fluid to be measured;
at least one measuring surface located in the housing and configured for contacting the fluid to be measured;
a signal generating device associated with the at least one measuring surface for generating signals related to the at least one property of the fluid;
a cleaning device operably associated with the housing, the cleaning device generating waves that are transmitted through the fluid to be measured and to the at least one measuring surface to thereby remove undesired material from the at least one measuring surface; and
an optical component located in the housing and including the at least one measuring surface to thereby define a first measuring surface, and wherein the signal generating device comprises an optical sensor module having a predetermined number of pixels positioned for receiving at least reflected radiant energy from the first measuring surface to thereby determine the at least one property of the fluid.

13. A system according to claim 12, and further comprising a fluid impedance measuring device located in the housing and having a pair of spaced electrodes defining respective second and third measuring surfaces located in a flow pathway of the fluid to be measured;
wherein the cleaning device is adapted to clean the first, second and third measuring surfaces via the fluid to be measured.

14. A system for determining at least one property of a fluid, the system comprising:
a housing for receiving the fluid to be measured;
at least one measuring surface located in the housing and configured for contacting the fluid to be measured;
a signal generating device associated with the at least one measuring surface for generating signals related to the at least one property of the fluid;
a cleaning device operably associated with the housing, the cleaning device generating waves that are transmitted through the fluid to be measured and to the at least one measuring surface to thereby remove undesired material from the at least one measuring surface; and an optical component located in the housing and including the at least one measuring surface to thereby define a first measuring surface, and wherein the signal generating device comprises an optical sensor positioned for receiving at least reflected radiant energy from the first measuring surface to thereby determine the at least one property of the fluid.

15. A system according to claim 14, and further comprising a fluid impedance measuring device located in the housing and having a pair of spaced electrodes defining respective second and third measuring surfaces located in a flow pathway of the fluid to be measured;

wherein the cleaning device is adapted to clean the first, second and third measuring surfaces via the fluid to be measured.

16. A method for cleaning a measuring surface associated with a first system for determining at least one property of a fluid to thereby assesses a suitability of using the fluid in a second system different from the first system, the method comprising:

providing the first system with a housing within which the measuring surface is located and a signal generating device associated with the measuring surface for generating signals related to the at least one property of the fluid;

flowing the fluid across the measuring surface to thereby measure the at least one fluid property in conjunction with the signal generating device;

cleaning the measuring surface by generating high frequency pressure waves with a transducer to produce micro cavitation bubbles that are transmitted through the flowing fluid and toward the measuring surface to thereby remove undesirable material from the measuring surface and clean the measuring surface when in contact with the fluid;

wherein the fluid is: 1) normally used in the second system; 2) measured via the at least one measuring surface and the signal generating device of the first system for determining the at least one property of the fluid and thus a suitability of the fluid for use in the second system; and 3) used as a cleaning fluid by the transducer in the first system to clean the measuring surface to accurately determine the at least one property of the fluid.

17. A method according to claim 16, and further comprising:

locating a shifted resonant frequency of the transducer by driving the transducer with a voltage wave form over a sweeping range of driving frequencies and monitoring a current of the voltage wave form to determine when the transducer reaches the shifted resonant frequency to thereby effectively clean the measuring surface independent of fluid type.

18. A method according to claim 17, and further comprising driving the transducer with the voltage wave form over the sweeping range of driving frequencies during a first period of time to create a single burst of swept frequencies.

19. A method according to claim 18, and further comprising repeating the single bursts of swept frequencies at discrete time intervals during a second period of time to thereby provide intermittent or continuous micro cavitation bubbles in the fluid directed toward the at least one measuring surface to thereby remove undesirable material from the at least one measuring surface upon collapse of the bubbles in the fluid for effective cleaning of the measuring surface.

20. A method according to claim 18, and further comprising monitoring the measuring surface with the signal generating device to determine whether a predetermined rate of change of the at least one fluid property over time is occurring to thereby quantify an effectiveness of the cleaning of the measuring surface.

21. A method according to claim 20, and further comprising determining a maximum cleanliness of the measuring surface by identifying when the predetermined rate of change of the at least one fluid property is no longer present.

* * * * *